United States Patent [19]

Starrett, Jr. et al.

[11] Patent Number: 5,945,561
[45] Date of Patent: Aug. 31, 1999

[54] RETINOID-LIKE COMPOUNDS

[75] Inventors: John E. Starrett, Jr., Middletown, Conn.; Kenneth M. Tramposch, E. Amherst, N.Y.; Xina Nair, E. Amherst, N.Y.; Peter R. Reczek, E. Amherst, N.Y.; Anna Ericsson, Quebec, Canada; Anne Marinier, Quebec, Canada; Alain Martel, Quebec, Canada; Fred C. Zusi, Hamden, Conn.

[73] Assignee: Bristol-Myers Squibb Company, Princeton, N.J.

[21] Appl. No.: 09/066,206

[22] Filed: Apr. 24, 1998

Related U.S. Application Data

[60] Provisional application No. 60/045,155, Apr. 30, 1997.

[51] Int. Cl.$^6$ .................................................. C07C 63/36
[52] U.S. Cl. ..................... 562/490; 562/465; 562/492; 560/10; 560/51; 560/53; 560/100; 560/102; 568/49; 568/58; 568/632; 568/733; 546/102; 546/285; 549/330; 514/544; 514/569
[58] Field of Search ..................... 562/490, 465, 562/492; 560/10, 51, 53, 100, 102; 568/49, 58, 632, 733; 546/10 L, 285; 549/330; 514/544, 569

[56] References Cited

U.S. PATENT DOCUMENTS

| | | |
|---|---|---|
| 4,876,381 | 10/1989 | Lang et al. . |
| 5,534,261 | 7/1996 | Rodgers et al. . |
| 5,618,839 | 4/1997 | Starrett, Jr. et al. . |

*Primary Examiner*—Paul J. Killos
*Attorney, Agent, or Firm*—David M. Morse

[57] ABSTRACT

Certain novel substituted (5,6)-dihydroanthracenyl compounds of the general formula

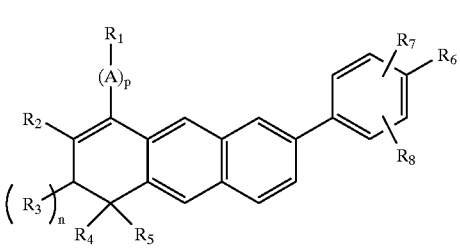

wherein A, n, p, $R_1$, $R_2$, $R_3$, $R_4$, $R_5$, $R_6$, $R_7$ and $R_8$ are as defined in the specification exhibit retinoid-like properties and are particularly useful in the prevention of post-surgical adhesions.

8 Claims, No Drawings

RETINOID-LIKE COMPOUNDS

This application claims benefit of Provisional Application 60/045,155, filed Apr. 30, 1997.

FIELD OF THE INVENTION

The present invention provides compounds having retinoid-like activity. More specifically, the compounds of the present invention are useful as antiinflammatory agents for chronic skin inflammatory diseases such as psoriasis and atopic dermatitis, as agents for the treatment of rheumatic diseases such as rheumatoid arthritis and as antitumor agents for the treatment of various tumors as well as non-malignant proliferative skin conditions. Additionally, the compounds are especially useful as agents for the minimization or prevention of post-surgical adhesion formation.

BACKGROUND OF THE INVENTION

Retinoic acid and its natural and synthetic analogs exert a wide variety of biological effects. They have been found to affect cellular growth and differentiation and are promising agents for the treatment of several cancers.

U.S. Pat. No. 5,618,839 discloses a series of substituted (5,6)-dihydronapthalenyl compounds of the formula

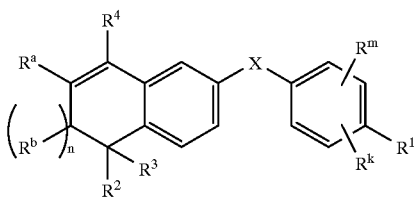

or nontoxic pharmaceutically acceptable salts, physiologically hydrolyzable esters or solvates thereof, in which
X is —O—CO—, —NH—CO—, —CS—NH—, —CO—O—, —CO—NH—, —COS—, —SCO—, —SCH$_2$—, —CH$_2$—CH$_2$—, —C≡C—, —CH$_2$—NH—, —COCH$_2$—, —NHCS—, —CH$_2$S—, —CH$_2$O—, —OCH$_2$—, —NHCH$_2$— or —CR$^5$=CR$^6$—;
R$^m$ and R$^k$ are independently hydrogen, halogen, C$_{1-6}$alkyl, hydroxy, C$_{1-6}$alkyloxy or nitro;
n is zero or one;
R$^4$ is —(CH$_2$)$_t$—Y, C$_{1-6}$alkyl, or C$_{3-6}$cycloalkyl;
R$^1$ is —CO$_2$Z, C$_{1-6}$alkyl, CH$_2$OH, —CONHR$^y$, or —CHO;
R$^2$ and R$^3$ are independently hydrogen or C$_{1-6}$alkyl;
R$^a$ and R$^b$ are independently hydrogen or C$_{1-6}$alkyl; but when n is one, R$^a$ and R$^b$ together can form a radical of the formula

Y is naphthyl or phenyl, both radicals can be optionally substituted with one to three same or different C$_{1-6}$alkyl or halogen;
Z is hydrogen or C$_{1-6}$alkyl;
R$^5$, R$^6$ and R$^y$ are independently hydrogen or C$_{1-6}$alkyl; and t is zero to six.

These compounds are reported to have retinoid-like activity and to be useful for preventing and/or treating various skin disorders such as acne, psoriasis and damage from irradiation, for treatment of various tumors and non-malignant proliferative skin diseases and for treatment of rheumatic diseases such as rheumatoid arthritis.

U.S. Pat. No. 5,534,261 discloses that retinoids, particularly all-trans retinoic acid, can be used to minimize or prevent adhesion formation following surgery.

SUMMARY OF THE INVENTION

The present invention provides novel compounds of formula I

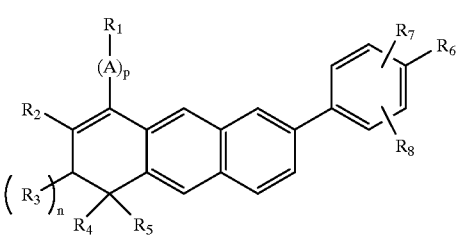

or nontoxic pharmaceutically acceptable salts, physiologically hydrolyzable esters or solvates thereof, in which
A is —O(CH$_2$)$_m$—, —S(O)$_q$(CH$_2$)$_m$—, —NR$_9$(CH$_2$)$_m$—, —C≡C—, —CR$_9$R$_{10}$, —CR$_9$=CR$_{10}$—, phenyl, naphthyl or heteroaryl, said phenyl, naphthyl or heteroaryl group being optionally substituted by 1 to 3 identical or different C$_{1-6}$alkyl, C$_{1-6}$alkoxy, halogen, —(CH$_2$)$_m$CO$_2$R$_9$,—(CH$_2$)$_m$CF$_3$, —(CH$_2$)$_m$CN, —(CH$_2$)$_m$N$_3$, —(CH$_2$)$_m$OR$_9$, —(CH$_2$)$_m$NR$_9$R$_{10}$, or —COR$_9$ groups;
R$_1$ is C$_{1-6}$alkyl, C$_{3-6}$cycloalkyl, —OSO$_2$CF$_3$, —OCOR$_{11}$, —OPO(OR$_{11}$)$_2$, halogen, aryl or heteroaryl, said aryl or heteroaryl group being optionally substituted by 1–3 identical or different C$_{1-6}$alkyl, C$_{1-6}$alkoxy, halogen, —(CH$_2$)$_a$CO$_2$R$_{11}$, —(CH$_2$)$_a$CF$_3$, —(CH$_2$)$_a$CN, —(CH$_2$)$_a$N$_3$, —(CH$_2$)$_a$OR$_{11}$, —(CH$_2$)$_a$NR$_{11}$R$_{12}$ or —COR$_{11}$ groups;
R$_2$ and R$_3$ are each independently hydrogen, C$_{1-6}$alkyl, C$_{2-6}$alkenyl or C$_{2-6}$alkynyl, but when n is 1, R$_2$ and R$_3$ together can form a radical of the formula

R$_4$ and R$_5$ are each independently hydrogen or C$_{1-6}$alkyl;
R$_6$ is —CO$_2$R$_{13}$, —C$_{1-6}$alkyl, —CH$_2$OH, —CONHR$_{13}$, —SO$_3$H, —PO$_3$H or —CHO;
R$_7$ and R$_8$ are each independently hydrogen, halogen, C$_{1-6}$alkyl, hydroxy, C$_{1-6}$alkyloxy, —CN, —N$_3$ or nitro;
R$_9$, R$_{10}$, R$_{11}$ and R$_{12}$ are each independently hydrogen, C$_{1-6}$alkyl or trifluoromethyl;
R$_{13}$ is hydrogen, C$_{1-6}$alkyl, allyl, benzyl, p-methoxybenzyl, trichloroethyl or trimethylsilylethyl;
n and p are 0 or 1; m, q and a are 0 to 2.

Also provided by this invention is a method for treating in a host animal, preferably a mammal, one or more of the diseases selected from the group consisting of chronic skin inflammatory diseases such as psoriasis and atopic dermatitis, rheumatic diseases such as rheumatoid arthritis, malignant tumors and non-malignant proliferative skin diseases which comprises administering to said host an effective therapeutic amount of a compound of formula I or a pharmaceutical composition thereof.

In another aspect the present invention provides a method for the minimization or prevention of a post-surgical adhesion formation between organ surfaces, comprising administering to an animal host an effective amount of a compound of formula I for a period of time sufficient to permit tissue repair. Such method is applicable to all living animals. The preferred host is a mammal and the most preferred host is a human.

In yet another aspect, the present invention provides a pharmaceutical composition comprising a therapeutically effective amount of a compound of formula I and a pharmaceutically acceptable carrier.

DETAILED DESCRIPTION OF THE INVENTION

The present invention relates to a compound of formula I

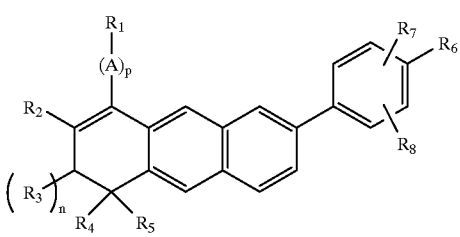

or nontoxic pharmaceutically acceptable salts, physiologically hydrolyzable esters or solvates thereof, in which A is —O(CH$_2$)$_m$—, —S(O)$_q$(CH$_2$)$_m$—, —NR$_9$(CH$_2$)$_m$—, —C≡C—, —CR$_9$R$_{10}$, —CR$_9$=CR$_{10}$—, phenyl, naphthyl or heteroaryl, said phenyl, naphthyl or heteroaryl group being optionally substituted by 1 to 3 identical or different C$_{1-6}$alkyl, C$_{1-6}$alkoxy, halogen, —(CH$_2$)$_m$CO$_2$R$_9$, —(CH$_2$)$_m$CF$_3$, —(CH$_2$)$_m$CN, —(CH$_2$)$_m$N$_3$, —(CH$_2$)$_m$OR$_9$, —(CH$_2$)$_m$NR$_9$R$_{10}$, or —COR$_9$ groups;

R$_1$ is C$_{1-6}$alkyl, C$_{3-6}$cycloalkyl, —OSO$_2$CF$_3$, —OCOR$_{11}$, —OPO(OR$_{11}$)$_2$, halogen, aryl or heteroaryl, said aryl or heteroaryl group being optionally substituted by 1–3 identical or different C$_{1-6}$alkyl, C$_{1-6}$alkoxy, halogen, —(CH$_2$)$_a$CO$_2$R$_{11}$, —(CH$_2$)$_a$CF$_3$, —(CH$_2$)$_a$CN, —(CH$_2$)$_a$N$_3$, —(CH$_2$)$_a$R$_{11}$, —(CH$_2$)$_a$NR$_{11}$R$_{12}$ or —COR$_{11}$ groups;

R$_2$ and R$_3$ are each independently hydrogen, C$_{1-6}$alkyl, C$_{2-6}$alkenyl or C$_{2-6}$alkynyl, but when n is 1, R$_2$ and R$_3$ together can form a radical of the formula

;

R$_4$ and R$_5$ are each independently hydrogen or C$_{1-6}$alkyl;
R$_6$ is —CO$_2$R$_{13}$, —C$_{1-6}$alkyl, —CH$_2$OH, —CONHR$_{13}$, —SO$_3$H, —PO$_3$H or —CHO;
R$_7$ and R$_8$ are each independently hydrogen, halogen, C$_{1-6}$alkyl, hydroxy, C$_{1-6}$alkyloxy, —CN, —N$_3$ or nitro;
R$_9$, R$_{10}$, R$_{11}$ and R$_{12}$ are each independently hydrogen, C$_{1-6}$alkyl or trifluoromethyl;
R$_{13}$ is hydrogen, C$_{1-6}$alkyl, allyl, benzyl, p-methoxybenzyl, trichloroethyl or trimethylsilylethyl;
n and p are 0 or 1; m, q and a are 0 to 2.

In the present application, the numbers in subscript after the symbol "C" define the number of carbon atoms a particular group can contain. For example, C$_{1-6}$alkyl refers to straight and branched chain alkyl groups with one to six carbon atoms. Thus, C$_{1-6}$alkyl may be methyl, ethyl, n-propyl, isopropyl, n-butyl, t-butyl, n-pentyl, n-hexyl, 3-methylpentyl, etc. and C$_{3-6}$ cycloalkyl may be cyclopropyl, cyclobutyl, cyclopentyl or cyclohexyl. The term "alkenyl" defines a carbon chain having at least one double bond. For example, C$_{2-6}$ alkenyl refers to a straight or branched chain of two to six carbons bearing at least one double bond, for example, ethenyl, 1-methyl-ethenyl, 1- or 2-propenyl, 1-methyl-1-propenyl, 1-methyl-2-propenyl, 1,1-dimethyl-2-propenyl, 2-methyl-2-propenyl, 1-, 2- or 3-butenyl, 1-methyl-1-butenyl, 2-methyl-1-butenyl, 3-methyl-1-butenyl, 3,3-dimethyl-1-butenyl, 1,2,3-dimethyl-1-butenyl, 1-methyl-2-butenyl, 1,1-dimethyl-2-butenyl, 2-methyl-2-butenyl, 3-methyl-2-butenyl, 1,3-butadienyl, 1,3-dimethyl-1,3-butadienyl, 1-, 2-, 3- or 4-pentenyl etc. The term "alkynyl" defines a carbon chain having at least one triple bond. For example, C$_{2-6}$ alkynyl refers to a straight or branched chain of two to six carbons bearing at least one triple bond, for example, ethynyl, 1- or 2-propynyl, 1-methyl-2-propynyl, 1,1-dimethyl-2-propynyl, 1-, 2- or 3-butynyl, 3-methyl-1-butynyl, 3,3-dimethyl-1-butynyl, 1-methyl-2-butynyl, 1,1-dimethyl-2-butynyl, 1-, 2-, 3, or 4-pentynyl etc.

The term "halogen" refers to fluorine, chlorine, bromine or iodine.

The term "aryl" as used herein and in the text includes mono-, bi- and polycyclic aromatic groups such as phenyl, naphthyl, anthracyl, phenanthryl, biphenyl, binaphthyl etc. The phenyl, naphthyl and biphenyl groups are preferred.

The term "heteroaryl" as used herein includes mono-, bi- and polycyclic aromatic heterocyclic groups containing 1–4 O, N or S atoms; preferred are 5- or 6-membered heterocyclic groups such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl, pyrazolyl, etc. and fused 5,6-membered and 6,6-membered aromatic heterocyclic groups such as benzofuranyl, isobenzofuranyl, benzothienyl, indolyl, isoindolyl, indazolyl, indolizinyl, isoquinolyl, quinolyl, naphthyridinyl, quinoxalinyl, quinazolinyl, pteridinyl etc. The thienyl, furyl, imidazolyl, pyridyl, pyrimidinyl, benzofuranyl, benzothienyl, indolyl, isoquinolyl and quinolyl groups are preferred.

A preferred embodiment of the present invention comprises a compound of the formula

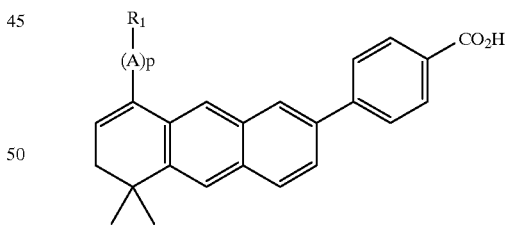

wherein A is —S(O)$_q$(CH$_2$)$_m$, —C≡C—, —CR$_9$R$_{10}$, —CR$_9$=CR$_{10}$—, phenyl, naphthyl or heteroaryl, said phenyl, naphthyl or heteroaryl group being optionally substituted by 1 to 3 identical or different C$_{1-6}$alkyl, C$_{1-6}$alkoxy, halogen, —(CH$_2$)$_m$CO$_2$R$_9$, —(CH$_2$)$_m$CF$_3$, —(CH$_2$)$_m$CN, —(CH$_2$)$_m$N$_3$, —(CH$_2$)$_m$OR$_9$, —(CH$_2$)$_m$NR$_9$R$_{10}$, or —COR$_9$ groups;

R$_1$ is C$_{1-6}$alkyl, C$_{3-6}$cycloalkyl, —OSO$_2$CF$_3$, —OCOR$_{11}$, —OPO(OR$_{11}$)$_2$, halogen, aryl or heteroaryl, said aryl or heteroaryl group being optionally substituted by 1–3 identical or different C$_{1-6}$alkyl, C$_{1-6}$alkoxy, halogen, —(CH$_2$)$_a$CO$_2$R$_{11}$, —(CH$_2$)$_a$CF$_3$, —(CH$_2$)$_a$CN, —(CH$_2$)$_a$N$_3$, —(CH$_2$)$_a$OR$_{11}$, —(CH$_2$)$_a$NR$_{11}$R$_{12}$ or —COR$_{11}$ groups;

$R_9$, $R_{10}$, $R_{11}$ and $R_{12}$ are each independently hydrogen, $C_{1-6}$alkyl or trifluoromethyl;

$R_{13}$ is hydrogen, $C_{1-6}$alkyl, allyl, benzyl, p-methoxybenzyl, trichloroethyl or trimethylsilylethyl;

p is 0 or 1; m, q and a are 0 to 2; or a nontoxic pharmaceutically acceptable salt, physiologically hydrolyzable ester or solvate thereof.

Another preferred embodiment of the present invention comprises the compound of the formula

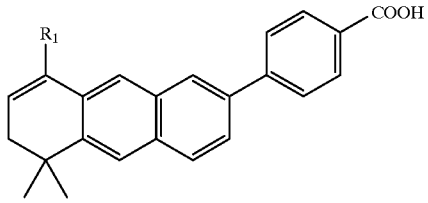

wherein $R_1$ is phenyl, p-methoxyphenyl, p-hydroxyphenyl, p-methylphenyl, 3,3-dimethyl-1-butyn-1-yl, tert-butylthio, m-hydroxyphenyl, 2-furanyl, 3-pyridinyl, or a nontoxic pharmaceutically acceptable salt, physiologically hydrolyzed ester or solvate thereof.

In another aspect, the present invention provides novel intermediates of the formula II

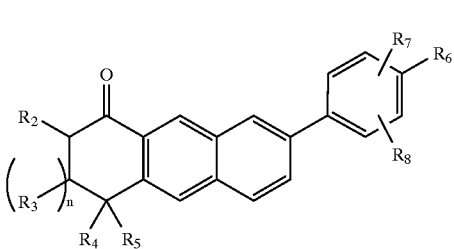

wherein $R_2$ and $R_3$ are each independently hydrogen, $C_{1-6}$alkyl, $C_{2-6}$alkenyl or $C_{2-6}$alkynyl, but when n is 1, $R_2$ and $R_3$ together can form a radical of the formula

$R_4$ and $R_5$ are each independently hydrogen or $C_{1-6}$alkyl;
$R_6$ is —$CO_2R_{13}$, —$C_{1-6}$alkyl, —$CH_2OH$, —$CONHR_{13}$, —$SO_3H$, —$PO_3H$ or —CHO;
$R_7$ and $R_8$ are each independently hydrogen, halogen, $C_{1-6}$alkyl, hydroxy, $C_{1-6}$alkyloxy, —CN, —$N_3$ or nitro;
$R_{13}$ is hydrogen, $C_{1-6}$alkyl, allyl, benzyl, p-methoxybenzyl, trichloroethyl or trimethylsilylethyl; and
n is 0 or 1.

Some compounds of formula I may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine, or the like pharmaceutically acceptable amines.

When a compound of formula I contains a carboxy group, it can form physiologically hydrolyzable esters which serve as prodrugs by being hydrolyzed in the body to yield formula I compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, benzyl, 4-methoxybenzyl, indanyl, phthalidyl, methoxymethyl, $C_{1-6}$alkanoyloxy, $C_{1-6}$alkyl, e.g. acetoxymethyl, pivaloyloxymethyl or propionyloxymethyl, $C_{1-6}$alkoxycarbonyloxy, $C_{1-6}$alkyl, e.g. methoxycarbonyloxymethyl or ethoxycarbonyloxymethyl, glycyloxymethyl, phenylglycyloxymethyl, (5-methyl-2-oxo-1-3-dioxolen-4-yl)-methyl and other well-known physiologically hydrolyzable esters used, for example, in the penicillin and cephalosporin arts. Such esters are prepared by conventional techniques known in the art.

The term "organ surface" is intended to encompass any internal organ of a living animal including but not limited to the uterus, intestines, liver, kidneys, heart and lungs.

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The synthesis of a compound of formula I can be accomplished by a wide variety of methods using conventional starting materials and processes. The synthetic schemes and specific examples that follow are only intended for the purpose of illustration and are not to be construed as limiting in any manner preparation of compounds of the present invention by other methods.

An illustrative reaction scheme for making a representative compound of the present invention is shown below and Example 1 below describes a typical synthesis:

SCHEME 1

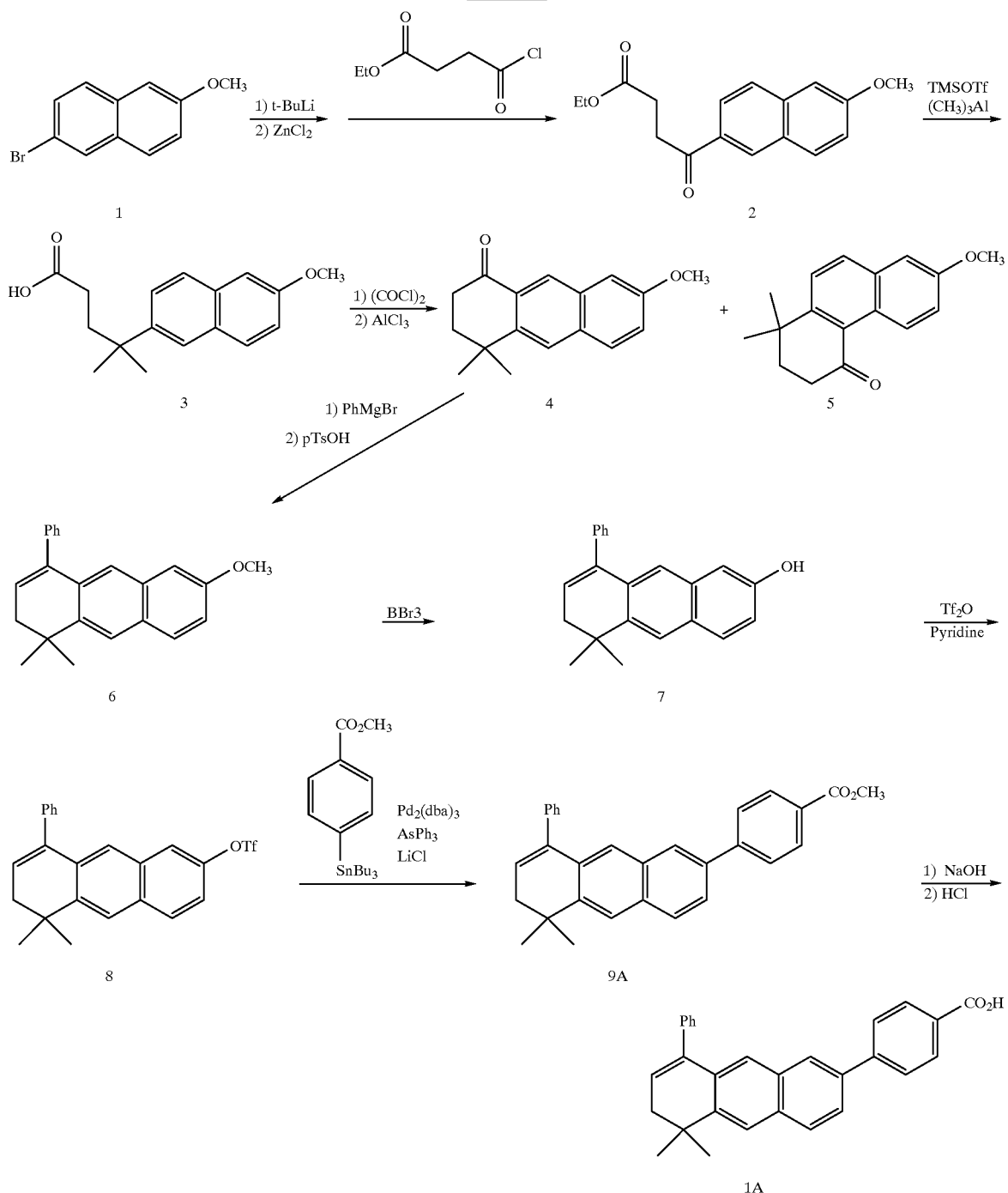

TMSOTf = trimethylsilyl triflate
pTSOH = p-toluenesulfonic acid
Tf$_2$O = triflic anhydride
AsPh$_3$ = triphenyl arsine
Pd$_2$(dba)$_3$ = tris(dibenzylideneacetone)$_3$dipalladium(O)

Bromonaphthalene 1 can be metalated with an organolithium such as t-butyl lithium to provide the lithiated naphthalene, which can then be treated with zinc chloride to afford the corresponding naphthyl zinc analog. Treatment of the naphthyl zinc with an activated carboxylic acid such as succinyl chloride gave ketonaphthalene 2. Using the method of Kim, et al. (Tet. Lett., 1994, 35, 3017–3020), treatment of keto-ester 2 with trimethylsilyl triflate and trimethyl aluminum incorporated the gem-dimethyl functionality to give 3. The carboxylic acid was then activated as its acid chloride following treatment with oxalyl chloride. Treatment of the acid chloride with a Lewis acid such as trimethyl aluminum afforded anthracenone 4 as well as phenanthrenone 5. Treatment of ketone 4 with a Grignard reagent such as phenyl magnesium bromide, followed by dehydration of the resulting tertiary alcohol with an acid such as p-toluenesulfonic acid, provided phenyl anthracene 6. Alcohol 7 was prepared by dealkylation of methyl ether 6 under standard conditions such as treatment with boron tribromide. The alcohol was then triflated with triflic anhydride to give triflate 8. Palladium-catalyzed coupling of triflate 8 with methyl-4-tri-n-butylstannyl benzoate (the stannyl benzoate may be prepared by the method of Hylarides, et al. as described in *J. Organomet. Chem.*, 1989, 367, 259–265) gave bi-aryl adduct 9 which was hydrolyzed with a base such as sodium hydroxide give acid 10 after acidic workup.

Alternatively, a second route was developed for making other representative compounds of the present invention using a late intermediate. This is illustrated in Scheme 2. 7-Methoxytetralone 10 was treated with a base such as sodium hydride to generate the enolate which was then reacted with diethylcarbonate. The resulting β-ketoester was then alkylated in presence of a base such as sodium ethoxide and ethyl bromobutyrate. Acid 11 was obtained after saponification and decarboxylation using the usual conditions. Subsequently, aromatization of the tetralone 11 was performed by preparing the phenylthioenol ether of the ketone using thiophenol in acidic conditions such as hydrochloric acid followed by oxidation of the resulting dihydronaphthalene nucleus with preferably 2,3-dichloro-5,6-dicyano-1,4-benzoquinone (DDQ) to give 12.

Incorporation of the gem-alkyl groups at position 5 was performed by a Grignard reaction and the resulting carbinol was cyclized under Friedel-Crafts conditions using preferably sulfuric acid. Treatment of the tetrahydroanthracene 13 with Raney nickel followed by removal of the methyl protecting group with preferably boron tribromide gave the tetrahydroanthracenol which was converted to the corresponding triflate 14 using triflic anhydride and pyridine. The benzoate side-chain was then introduced by a palladium-catalyzed coupling with methyl-4-tri-n-butylstannyl benzoate using conditions known in the art and the substituted anthracenone 15 was obtained after benzylic oxidation with preferably pyridinium dichromate and tert-butyl hydroperoxide. Conversion of the ketone to the corresponding enol triflate under the usual conditions afforded the common late intermediate triflate 16. Various cross-coupling type reactions may then be performed with this enol triflate to introduce the various side-chains at position 8. The resulting 8-substituted dihydroanthracene compound of type 9 was then saponified in the conditions known in the art to give the desired compound of formula I.

SCHEME 2

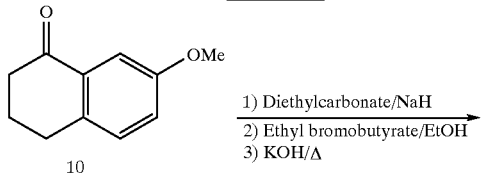

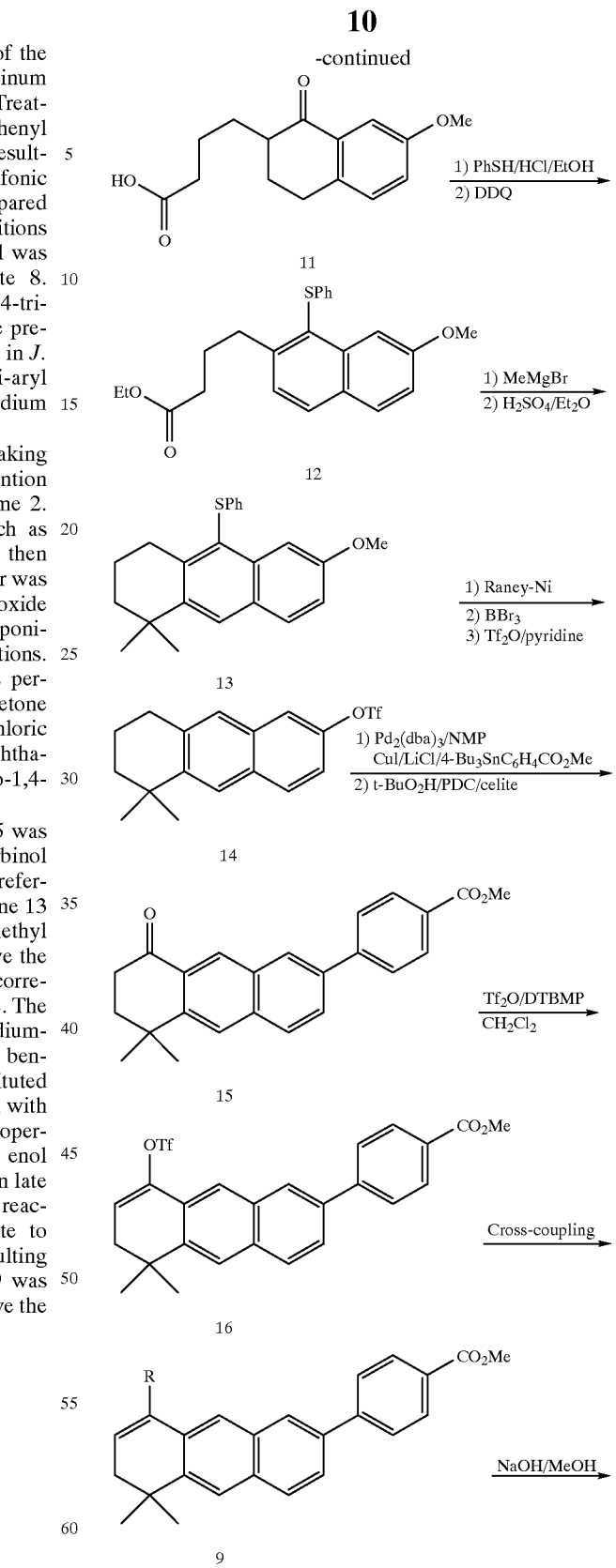

-continued

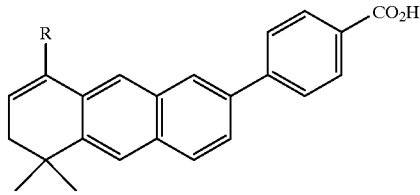

I

DDQ = 2,3-dichloro-5,6-dicyano-1,4-benzoquinone
PDC = pyridinium dichromate
NMP = N-methylpyrolidinone
DTBMP = 2,6-di-t-butyl-4-methyl-pyridine A representative compound of the present invention, i.e. that of Example 1, was tested for its antitumor activity and its ability to prevent post-surgical adhesions.

Prevention of Surgical Adhesions

Models of peritoneal adhesions induced by surgical trauma have been used to predict the clinical activity of a number of marketed anti-adhesion barrier devices. One such model is the trauma-induced caecal adhesion model in rats. The compound of Example 1 was used with this model to demonstrate efficacy.

Adult female Wistar rats were used in our studies. The trauma induction was carried out using aseptic conditions in animals anesthetized with a mixture of Ketamine (100 mg/kg) and Rompun (10 mg/kg) given IP. A 2 cm midline abdominal incision was made and the caecum was exteriorized. Both sides of the caecum were abraded with a dry gauze until there was evidence of punctate bleeding. After replacing the organ in the abdominal cavity, the incision was closed. Trauma to the caecum produces fibrous scar tissue or adhesions to adjacent organs, peritoneal wall, or the omentum. Animals were treated with test compound orally. Oral treatments were administered once daily for up to 7 days.

On the seventh postoperative day, the animals were sacrificed and the peritoneal cavity was exposed and examined for adhesions. Three criteria that were used to evaluate the adhesions are: severity of the adhesions, extent or area of the ceacum involved with adhesions and the number of adhesions formed in each animal. Statistical analysis of the data was performed using students' T test. The following scoring system was used:

| Grade | Description |
| --- | --- |
| 0 | = no adhesions |
| 1.0 | = easily separable, filmy, non-vascularized adhesions covering 25% of the caecum; |
| 2.0 | = dense adhesions separated by blunt dissection and involving 50% of the caecum; |
| 3.0 | = dense, fibrous, vascularized adhesions requiring sharp dissection and covering 75% of the caecum; |
| 4.0 | = severe, dense, vascularized adhesions unable to separate without tearing the adjacent membranes and covering greater than 75% of the caecum. |

The Dose Dependent Effect of Orally Dosed Test Compound on Trauma-induced Ceacal Adhesions in Female Wistar Rat

| Treatment (1 × daily for 7 days) | N | Dose | Mean number of adhesions/rat +/− SD | Mean Adhesion Severity/Rat +/− SD |
| --- | --- | --- | --- | --- |
| Vehicle (peanut oil) | 5 | 4 ml/kg | 15.4 +/− 4.8 | 39.2 +/− 15 |
| Compound of Ex. 1 | 5 | 3 mg/kg | 14.6 +/− 2.7 | 36 +/− 7.0 |
| Compound of Ex. 1 | 5 | 10 mg/kg | 12.2 +/− 1.6 | 30.2 +/− 5.5 |
| Compound of Ex. 1 | 5 | 25 mg/kg | 6.8 +/− 2.4* | 14.8 +/− 5.6* |

*p = 0.03

As shown above, the compounds of the present invention are useful in the prevention of post-surgical adhesions.

Antitumor Activity

HL60 cells were evaluated for the effects of retinoic acid and the compound of Example 1 for both differentiation and apoptosis end points by the method described in *Molecular and Cellular Biology*, 15 3540–3551 (1995). Cells were grown in culture for times up to 9 days in the presence of 1 $\mu$m all-trans retinoic acid (4-RA) or 1 $\mu$m compound of Example 1. At the end of each day of the culture period, cells were washed and stained with NBT (nitro blue tetrazolium) and counted. NBT staining reveals distinct changes in nuclear morphology and can easily be compared with treatment by t-RA or compound of Example 1. The $EC_{50}$ is defined as the culture day necessary to convert cells into a differentiated or apoptosed phenotype and is given below in Table I. The compound of Example 1 is comparable to t-RA in this assay.

TABLE I

| Differentiation and Apoptosis of HL6O cells | |
| --- | --- |
| Compound | $EC_{50}$ |
| tRA | 3.2 days |
| Compound of Example 1 | 6.0 days |

Thus, the compounds of the present invention are useful in the treatment of tumors in mammals.

The compounds of the present invention are also useful for treating a host animal, preferably a mammal and most preferably a human, for chronic skin inflammatory diseases, rheumatic diseases and non-malignant proliferative skin conditions. In such cases an effective therapeutical amount of a compound of claim 1 or a pharmaceutical composition thereof is administered to said host animal in the same manner as other retinoid compounds.

For prevention of surgical adhesions, a compound of the present invention may be administered by a variety of systemic and local methods. The compounds may be administered orally, by intravenous injection, by intramuscular injection or by intracavity instillation. The general range of doses will depend on the efficacy of each compound and the intended route, but is expected to be from 0.1 mg/kg to 100 mg/kg with a preferred range of 1 to 25 mg/kg. Preferred routes of administration are oral administration or direct administration (intracavity instillation) to a site of surgical activity on an organ surface.

The term of administration may vary depending upon a number of factors which would be readily appreciated by those skilled in the art. In general, administration of a compound of the present invention should be effected 12–48 hours prior to the time of surgery and for at least 24–48 hours post-surgery. In general the compound may be administered from 72 hours prior to surgery and continue up to 2 weeks after surgery and preferably for a period 12 hours prior to surgery and continuing 48 hours after surgery.

For intracavity administration the compound can be administered in a suitable vehicle such as 5% dextrose in water adjusted to a pH to assure complete salt formation. However it is understood that many other single dose delivery systems could be contemplated by those skilled in the art including microcapsules, microspheres, liposomes, viscous instilates, and polymeric delivery materials.

The compounds of formula I above may be used topically or systemically, as anticancer agents and in the treatment, amelioration or prevention of the skin disorders and rheumatic illnesses (including rheumatoid arthritis) described in U.S. Pat. No. 5,618,839. In this regard they may be used for therapy in animals, including humans, of premalignant epithelial cell lesions, as a prophylaxis against tumor promotion in epithelial cells and treatment for dermatoses such as ichthyoses, follicular disorders, benign epithelial disorders and other proliferative skin diseases such as psoriasis, eczema, atopic dermatitis, non-specific dermatosis and the like. They may also be used in reversing and preventing the effects of irradiation damage to skin. When used for the above purposes, they will usually be formulated with a pharmaceutically acceptable liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles (excipients) in the pharmaceutical formulation art. The carrier may be organic or inorganic in nature. Examples of pharmaceutically acceptable carriers that may be used to formulate a compound of formula I are water, gelatin, lactose, starch, mineral oil, cocoa butter, dextrose, sucrose, orbital, mannitol, gum acacia, alginates, cellulose, talc, magnesium stearate, polyoxyethylene sorbitan monolaurate, and other commonly used pharmaceutical carries. In addition to a compound of formula I and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I are administered will vary according to the dosage form, mode of administration, the condition being treated and particulars of the patient being treated. Accordingly, optimal therapeutic concentrations will be best determined at the time and place through routine experimentation.

In the treatment of dermatoses, it will generally be preferred to administer the drug topically, though in certain cases oral administration may also be used. If the compounds according to the invention are used topically, it will be found that they exhibit a good activity over a very broad range of dilution; in particular, concentrations of the active compound or compounds ranging from 0.0005% to 2% by weight can generally be used. It is of course possible to use higher concentrations if this should become necessary for a particular application; however, the preferred concentration of active principle are from 0.002% to 1% by weight.

For topical administration the compounds of formula I are conveniently provided in the form of unguents, gels, creams, ointments, powders, dyeing compositions, solutions, suspension, emulsions, lotions, sprays, adhesive plasters and impregnated pads. The compounds according to the invention can be mixed with inert nontoxic, generally liquid or pasty, bases suitable for topical treatment. Preparation of such topical formulations are well described in the art of pharmaceutical formulations as exemplified, for example, Remington's Pharmaceutical Science, Edition 17, Mack Publishing Company, Easton, Pa. Other medicaments can be added to such formulation for such secondary purposes as treating skin dryness, providing protection against light; other medications for treating dermatoses, preventing infection, reducing irritation, inflammation and the like.

The compounds according to the invention can also be used enterally. Orally, the compounds according to the invention are suitable administered at the rate of 100 $\mu$g to 100 mg per day per kg of body weight. The required dose can be administered in one or more portions. For oral administration, suitable forms are, for example, tablets, pills, dragees, syrups, suspensions, emulsions, solutions, powders and granules; a preferred method of administration consists in using pills containing from 1 mg to about 1000 mg of active substance.

U.S. Pat. No. 4,876,381 issued on Oct. 24, 1989 to Lang et al. provides examples of formulations constituting gel, unguent, powder, cream, etc. The aforesaid U.S. patent can be used as a guide to formulate a compound of formula I and is herein incorporated by reference in its entirety.

Isotretinoin (Accutane®) and etretinate (Tegison®) are used clinically to treat severe recalcitrant cystic acne and severe recalcitrant psoriasis, including the erythrodermica and generalized pustular types, respectively. Their mode of use is amply illustrated in the Physicians's Desk Reference, 47th Edition, 1993, published by Medical Economics Data. The compounds of formula I may also be used to treat severe recalcitrant psoriasis. In so doing, the compounds of the present invention may be used in a similar fashion to isotretinoin and etretinate; thus, the relevant sections on isotretinoin and etretinate in the Physician's Desk Reference will serve as a convenient guide which will obviate the need for any undue experimentation.

The compounds according to the invention can also be administered parenterally in the form of solutions or suspensions for intravenous or intramuscular perfusions or injections. In that case, the compounds according to the invention are generally administered at the rate of about 10 $\mu$g to 10 mg per day per kg of body weight; a preferred method of administration consists of using solutions or suspensions containing approximately from 0.01 mg to 1 mg of active substance per ml.

Several retinoids have been found to possess anti-tumor properties. Roberts, A. B. and Sporn, M. B. in *"The Retinoids"*, Sporn, M. B., Roberts, A. B., and Goodman, D. S., eds, 1984, 2 pp. 209–286, Academic Press, New York; Lippman, S. M., Kessler, J. F., and Meyskens, F. L., *Cancer Treat. Rep.,* 1987, 71, p. 391; ibid., p. 493. As used herein, the term "anti-tumor" includes both chemopreventive (prophylactic or tumor promotion inhibiting) and therapeutic (curative) use. For example, all-trans retinoic acid can be used to treat acute promyelocytic leukemia. Huang, M. Et al., *Blood,* 1988, 72 p. 567. Isotretinoin has been shown to be useful in prevention of second primary tumors in squamous-cell carcinoma of the head and neck. Hong, W. K. et al., *N. Engl. J. Med.,* 1990, 323 p. 795.

The compounds of formula I can be used in a substantially similar manner to retinoids for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on retinoids found to have anti-tumor properties. For example, for the prevention of second primary tumors with a compound of formula II in squamous-cell carcinoma of the head and neck, an oncologist may refer to the study by Hong, W. K. et al. in *N. Engl. J. Med.*, 1990, 323, p. 795. For treating acute promyelocytic leukemia, the oncologist may refer to the study by Huang, M. et al. in *Blood*, 1988, 72, p. 567.

DESCRIPTION OF SPECIFIC EMBODIMENTS

The specific examples which follows illustrate the synthesis of representative compounds of the present invention. The procedures may be adapted to variations in order to produce compounds within the scope of the invention but not specifically disclosed.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quarter (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value. All melting points were determined on a Gallenkamp melting point apparatus and were not corrected. Analytical grade solvents were used for reactions and chromatographies. Flash column chromatographies were performed on Merck silica gel 60 (230–400 Mesh) and Merck silica gel 60 $F_{254}$ 0.5 mm plates were used.

The following conventional abbreviations are used in the example:

Et=ethyl
Ph=phenyl
TM=trimethyl
Tf=triflate
DMF=dimethylformamide
THF=tetrahydrofuran
pTs=p-toluenesulfonic acid

EXAMPLE 1

4-(5,6-Dihydro-5,5-dimethyl-8-phenylantracen-2-yl)-benzoic acid (IA)

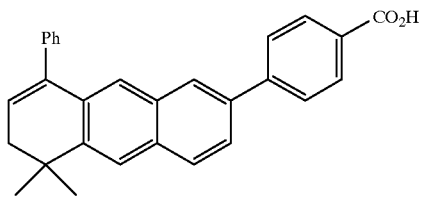

6-Methoxy-γ-oxonaphthalene-2-butanoic acid, ethyl ester (2).

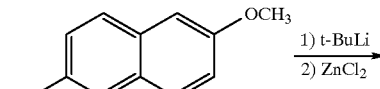

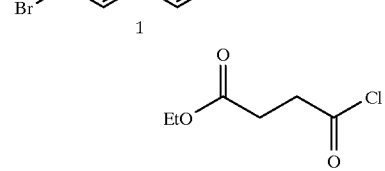

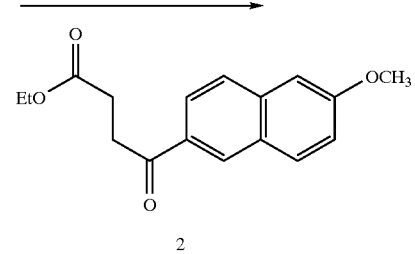

2

A suspension of 10.0 g (0.042 mol) of 2-bromo-6-methoxynaphthalene (1) (Aldrich) in 75 mL of ether was cooled to −78° C. To this mixture was added 52 mL (0.087 mol) of a 1.7 M solution of t-butyl lithium in pentane (Aldrich). After stirring for 10 minutes was added 42 ml (0.042 mol) of IM solution of zinc chloride in ether (Aldrich). A thick, white precipitate formed which was difficult to stir with a magnetic stir bar. The bath was removed and stirring became easier. After stirring for 90 minutes, the mixture was cooled to −78 and a solution of 6.3 mL (0.044 mol) of ethyl succinyl chloride in 10 mL of ether was added. The reaction was stirred for 20 minutes and the bath was removed and stirring was continued for 16 hrs.

The mixture was partitioned between 1 N HCl and ethyl acetate, resulting in some insoluble material at the interface between the layers. The organic layer was removed, dried over magnesium sulfate and stripped to dryness. The residue was recrystallized from 50 mL of methanol to give 3.2 g of the title compound as a white, crystalline solid. The insoluble material at the interface from the extraction was collected, treated with 1 N NaOH and extracted with ethyl acetate (2x) and ether (3x). The combined organic layer was evaporated to dryness to give 3.0 g of the title compound which was identical by TLC and NMR to the material from the methanol recrystallization. The two lots were combined to give a total of 6.1 g, 51% yield of the title compound 2.

IR (KBr, $cm^{-1}$) 2994,1732,1674,1620, 1484, 1390,1308, 1234, 1162; $^1$H NMR (300 MHz, $CDCl_3$) 1.26 (3H, t, J=7.1 Hz), 2.78 (2H, t, J=6.7 Hz), 3.40 (2H, t, J=6.7 Hz), 3.92 (3H, s), 4.15 (2H, q, J=7.1 Hz) 7.12 (1H, d, J=2.4), 7.17 (1H, dd, J=2.4, 8.9 Hz), 7.74 (1H, d, J=8.7 Hz), 7.83 (1H, d, J=8.9 Hz), 7.99 (1H, dd, J=1.8, 8.6 Hz), 8.41 (1H, d, J=1.3 Hz); MS m/e 287 (MH$^+$). Anal calcd. for $C_{17}H_{18}O_4$; C, 71.31, H, 6.34. Found: C, 71.03, H, 6.36.

6-Methoxy-γ,γ'-dimethylnaphthalene-2-butanoic acid (3).

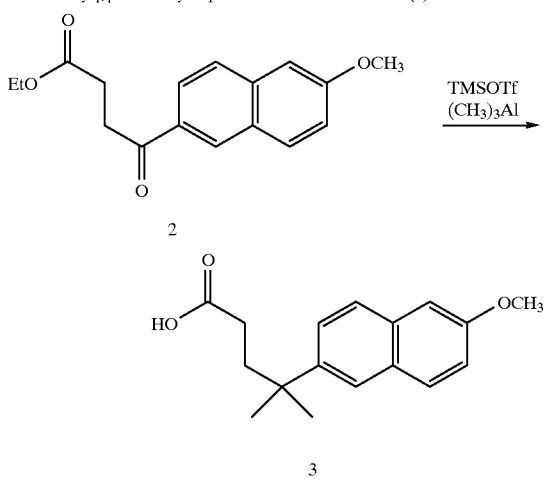

To a solution of 6.1 g (0.021 mol) of ketoester 2 in 100 mL of CH$_2$Cl$_2$ cooled in a methanol/ice bath was added 23 mL (0.046 mol) of trimethyl aluminum (Aldrich), followed by the dropwise addition of 4.6 mL (0.024 mol) of trimethylsilyltriflate (TMSOTf; Aldrich). The bath was allowed to melt and the reaction was stirred for 16 hrs. The reaction was treated with 1 N HCl (caution: vigorous gas evolution) and extracted with CH$_2$Cl$_2$. The organic layer was dried over magnesium sulfate and evaporated to dryness. The residue was partitioned between 1 N NaOH and ether. The organic layer was discarded and the basic layer was acidified with 1 N HCl and extracted with ether, and then ethyl acetate. The combined organic layer was dried over magnesium sulfate and evaporated to dryness to give 2.7 g of the title compound (37%).

IR (KBr, cm$^{-1}$) 2980, 1705, 1600, 1480, 1260, 1210; $^1$H NMR (300 MHz, CDCl$_3$) 1.41 (6H, s), 2.06 (4H, m), 3.91 (3H, s), 7.1 (2H, m), 7.45 (1H, dd, J=2.0, 8.5 Hz), 7.62 (1H, d, J=1.8 Hz), 7.69 (2H, d, J=8.5 Hz); MS m/e 273 (MH$^+$). Anal calcd. for C$_{17}$H$_{20}$O$_3$.0.25 H$_2$O; C, 74.97, H, 7.40. Found: C, 73.44, H, 7.46.

1,2,3,4-Tetrahydro-7-methoxy-4,4-dimethylanthracen-1-one (4).

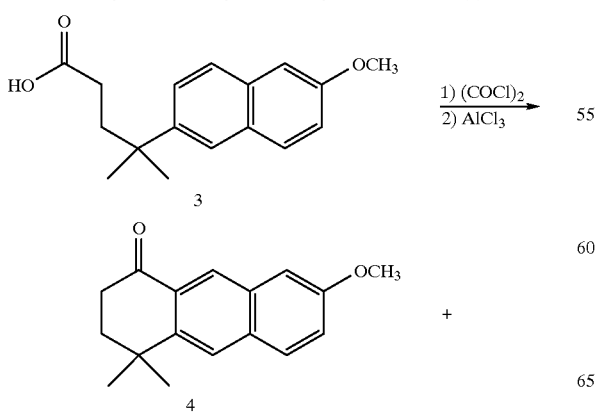

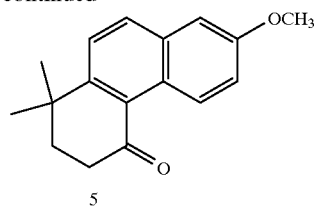

To a suspension of 2.4 g (8.82 mmol) of acid 3 in 50 mL of CH$_2$Cl$_2$ cooled to 0° C. was added 2.4 mL (27.5 mmol) of oxalyl chloride (Aldrich) and three drops of DMF (dimethylformamide). The reaction was stirred for 30 min., the ice bath was removed, and stirring was continued to 2 hrs. The solvents were removed in vacuo and the residue was dissolved in 75 mL of CH$_2$Cl$_2$. To this solution was added 2.35 g (17.6 mmol) of aluminum trichloride (Aldrich) and the mixture was stirred for 45 min. The reaction was carefully quenched with 1N HCl and extracted with ethyl acetate. The organic layer was dried over magnesium sulfate, evaporated to dryness and the residue was purified on a 45 mm flash chromatography column, eluting with hexane/ethyl acetate 9/1 to give the title compound, as well as a mixture of the title compound 4 and the regioisomer 1,2,3,4-tetrahydro-7-methoxy-1,1-dimethylphenanthren-4-one (5). The mixture was repurified under the same conditions, and the two lots of the title compound combined to give 0.44 g (20%) of product 4. An analytical sample was recrystallized from methanol and the structure was confirmed by single crystal X-ray analysis.

IR (KBr, cm$^{-1}$) 2980, 1685, 1635, 1595, 1235; $^1$H NMR (300 MHz, CDCl$_3$) 1.46 (6H, s), 2.09 (2H, d, J=8.1 Hz), 2.83 (2H, d, J=8.1 Hz), 3.91(3H, s), 7.21 (1H, s), 7.25 (1H, d, J=8.3 Hz), 7.72 (1H, br d, J=8.3 Hz), 7.75 (1H, s), 8.49 (1H, s); MS m/e 255 (MH$^+$). Anal calcd. for C$_{17}$H$_{18}$O$_2$; C, 80.28, H, 7.13. Found: C, 80.15, H, 6.97.

1,2-Dihydro-6-methoxy-1,1-dimethyl-4-phenylanthracen (6).

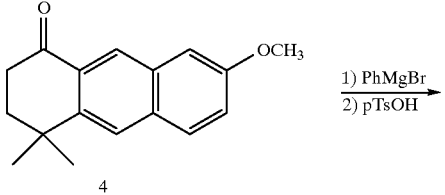

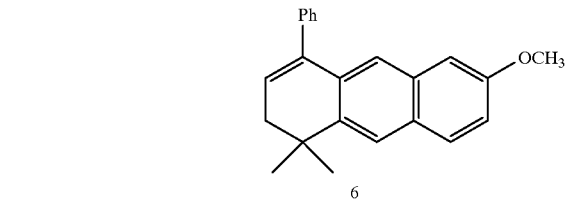

To a solution of 0.44 g (1.73 mmol) of ketone 4 dissolved in 15 mL of THF (tetrahydrofuran) and cooled to −78° C. was added 0.88 mL (2.64 mmol) of 3.0 M phenyl magnesium bromide (Aldrich). The mixture was stirred for 5 min., the bath was removed, and the reaction was stirred for an additional 90 min. To this was added 1 N HCl and the mixture was stirred for 15 min. and then extracted with ethyl acetate. The organic layer was dried over magnesium sulfate and evaporated to dryness. The residue was dissolved in 15 mL of benzene, 50 mg of pTsOH (p-toluenesulfonic acid)

was added, and the mixture was heated at 70° C. for 2 hrs. After cooling, the solvents were removed in vacuo and the residue purified on a 40 mm flash chromatography column, eluting with hexane/ethyl acetate 20/1 to give 0.33 g of the title compound 6 (61% yield).

$^1$H NMR (300 MHz, CDCl$_3$) 1.47 (6H, s), 2.43 (2H, d, J=4.7 Hz), 3.85 (3H, s), 6.09 (1H, t, J=4.8 Hz), 6.98 (1H, d, J=2.5 Hz), 7.10 (1H, dd, J=2.5, 6.3 Hz), 7.4 (6H,m), 7.7 (2H, m); MS m/e 315 (MH$^+$).

5,6-Dihydro-5,5-dimethyl-8-phenylanthracen-2-ol (7).

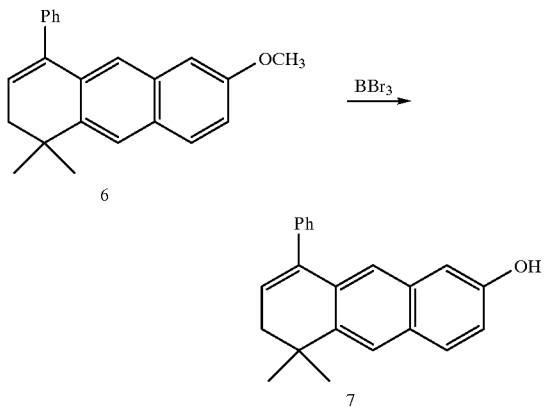

To a solution of 0.33 g (1.05 mmol) of methyl ether 6 in 10 mL of CH$_2$Cl$_2$ was added 5.25 mL (5.25 mmol) of 1 M boron tribromide in methylene chloride (Aldrich). After stirring for two hours, the reaction was treated with 1 N HCl and extracted with ethyl acetate. The organic layer was dried over magnesium sulfate, evaporated to dryness, and the residue was purified on a 35 mm flash chromatography column, eluting with hexane/ethyl acetate 4/1 to provide 0.31 g ( 100%) of the title compound 7.

$^1$H NMR (300 MHz, CDCl$_3$) 1.44 (6H, s), 2.41 (2H, d, J=4.7 Hz), 4.32 (1H, br s), 6.08 (1H, t, J=4.7 Hz), 6.93 (1H, d, J=2.2 Hz), 7.03 (1H, dd, J=2.5, 6.2 Hz), 7.30 (1H, s), 7.4 (5H, m), 7.6 (2H, m); MS m/e 301 (MH$^+$).

Trifluoromethanesulfonic acid, 5,6-dihydro-5,5-dimethyl-8-phenylanthracen-2-yl ester (8).

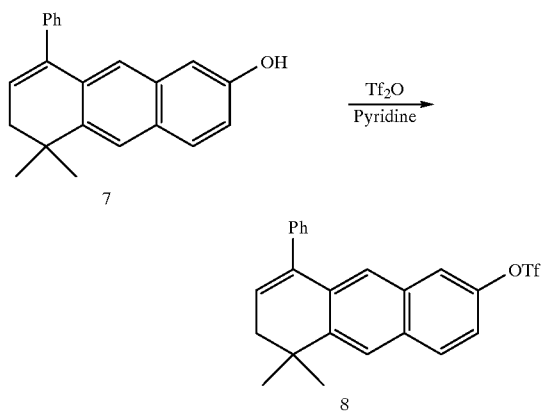

A solution of 0.31 g (1.03 mmol) of alcohol 7 in 10 mL of pyridine was cooled to 0° C. and treated with 0.38 mL (2.2 mmol) of triflic anhydride. The bath was removed and the reaction was stirred for 20 hrs, poured into 1 N HCl and extracted with ethyl acetate (2x). The combined organic layer was washed with 1 N HCl, dried over magnesium sulfate and evaporated to dryness to give 0.31 g of the title compound 8 (70% yield).

$^1$H NMR (300 MHz, CDCl$_3$) 1.46 (6H, s), 2.45 (2H, d, J=4.8 Hz), 6.14, (1H, t, J=4.8 Hz), 7.30 (1H, dd, J=2.5, 6.5), 7.4 (6H, m), 7.54 (1H, d, J=2.5 Hz), 7.81 (1H, s), 7.88 (1H, d, J=9.1 Hz); MS m/e 433 (MH$^+$).

4-(5,6-Dihydro-5,5-dimethyl-8-phenylanthracen-2-yl)benzoic acid, methyl ester (9).

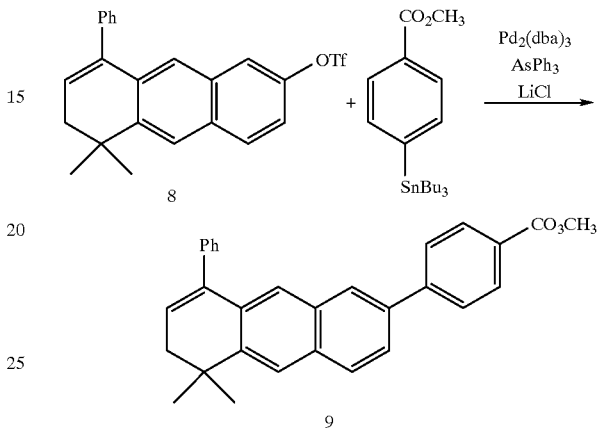

To a solution of 0.32 g (0.74 mmol) of triflate 8 in 5 mL of N-methyl-2-pyrrolidinone (NMP; note: after dissolving compounds in NMP, all solutions were degassed by bubbling in a stream of argon for 15 min. prior to using in the reaction) was added 13 mg (0.015 mmol) of tris (dibenzylideneacetone)3dipalladium(0) (Pd$_2$(dba)$_3$; Aldrich), 18 mg (0.06 mmol) of triphenyl arsine (Aldrich), and 93 mg (2.2 mmol) of lithium chloride (Mallinckrodt). The reaction was stirred for 10 min. and a solution of 0.34 g (0.89 mmol) of methyl-4-tri-n-butylstannyl benzoate in 1 mL of NMP was added. After stirring at 50° C. for 26 hrs, an additional 0.2 g (0.5 mmol) of aryl tin, dissolved in 0.5 mL of NMP, was added and the reaction was stirred at 50° C. for an additional 24 hrs.

The reaction was cooled and treated with 2 mL of aqueous KF. After stirring for 20 min., the mixture was filtered and washed with ethyl acetate. The filtrate was diluted with 150 mL of ethyl acetate, washed with water, dried over magnesium sulfate and evaporated to dryness. The residue was purified on a 35 mm flash column, eluting with hexane/ethyl acetate 9/1 to provide 0.25 g (81%) of the title compound 9.

$^1$H NMR (300 MHz, CDCl$_3$) 1.46 (6H, s), 2.45 (2H, d, J=4.8 Hz), 3.94, (3H, s), 6.14, (1H, t, J=4.8 Hz), 7.3–8.2 (14H, m); MS m/e 419 (MH$^+$). Anal calcd. for C$_{30}$H$_{26}$O$_2$; C, 86.09 H, 6.26. Found: C, 85.57, H, 6.42.

4-(5,6-Dihydro-5,5-dimethyl-8-phenylanthracen-2-yl)benzoic acid (IA).

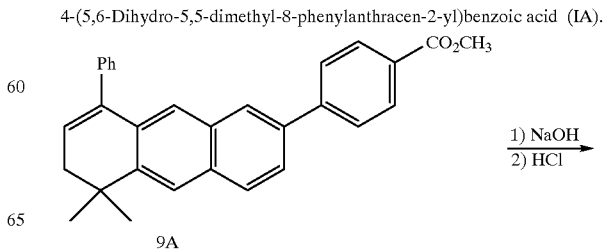

-continued

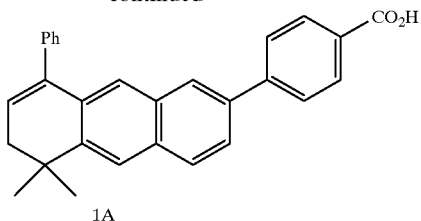

1A

Suspended 0.15 g (0.36 mmol) of ester 9 in 5 mL of ethanol, added 2 mL of 10 N NaOH and heated at 70° C. for 2 hrs. Cooled, diluted with 100 mL of 1 NHCl, collected solid, washed with water and dried to provide 0.13 g of the title compound IA, mp. 279–281° C.

IR (KBr, cm$^{-1}$) 3440, 2958, 1688,1608, 1396, 1282; $^1$H NMR (300 MHz, DMSO-d$_6$) 1.40 (6H, s), 2.39 (2H, d, J=4.6), 3.34 (1H, br s), 6.08 (1H, t, J=4.6), 7.3–8.0 (13H, m), 8.08 (1H, br s); MS m/e 405 (MH$^+$). Anal calcd. for $C_{29}H_{24}O_2 \cdot H_2O$; C, 82.50 H, 5.92. Found: C, 82.43, H, 6.20.

EXAMPLE 2

4-(5,6-Dihydro-5,5-dimethyl-8-(4-methoxy-phenyl)-anthracen-2-yl)-benzoic acid (IB)

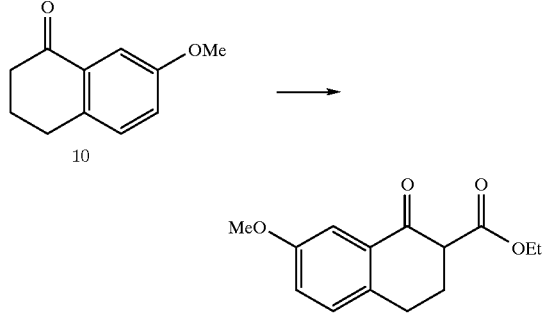

2-(Ethoxycarbonyl)-7-methoxy-1-oxo-1,2,3,4-tetrahydronaphthalene

7-Methoxy-1-oxo-1,2,3,4-tetrahydronaphthalene 10 (25.0 g, 0.139 mol) was dissolved in anhydrous THF (500 mL) at room temperature and sodium hydride (13.1 g, 0.518 mol) followed by diethyl carbonate (35.9 mL, 0.418 mol) were added. The reaction mixture was refluxed for 18 h. After cooling down to 0° C., the reaction mixture was quenched by dropwise addition of acetic acid (50 mL). Benzene was added, and the solvent was evaporated. After addition of diethylether, the organic phase was washed with brine, dried over magnesium sulfate and evaporated to give a brown solid. The solid crude product was finally washed with EtOAc/hexane 95/5 to give 35 g (100%) of the title material as a white solid which was found to be a 1:1 mixture of the enol and keto forms.

IR (KBr, cm$^{-1}$): 3100–2834 (aliphatic, aromatic), 1739 (carbonyl), 1684 (carbonyl), 1647 (carbonyl), 1597, 1571, 1498, 1398, 1377, 1326, 1302, 1225, 1179, 1029; $^1$H NMR (400 MHz, CDCl$_3$): 12.52 (s, 1H), 7.52 (d, J=2.8 Hz, 1H), 7.35 (d, J=2.4 Hz, 1H), 7.16 (d, J=8.4 Hz, 1H), 7.08 (d, J=8.0 Hz, 1H), 7.07 (dd, J=8.4, 2.8 Hz, 1H), 6.89 (dd, J=8.0, 2.4 Hz, 1H), 4.31–4.21 (m, 4H), 3.83 (s, 3H), 3.83 (s, 3H), 3.57 (dd, J=10.4, 4.8 Hz, 1H), 3.03–2.87 (m, 2H), 2.74 (dd, J=15.6, 7.2 Hz, 2H), 2.55 (dd, J=8.4, 8.4 Hz, 2H), 2.51–2.43 (m, 1H), 2.38–2.32 (m, 1H), 1.35 (t, J=7.2 Hz, 3H), 1.29 (t, J=7.2 Hz, 3H).

4-(7-Methoxy-1-oxo-1,2,3,4-tetrahydronaphthalen-2-yl)-butyric acid (11)

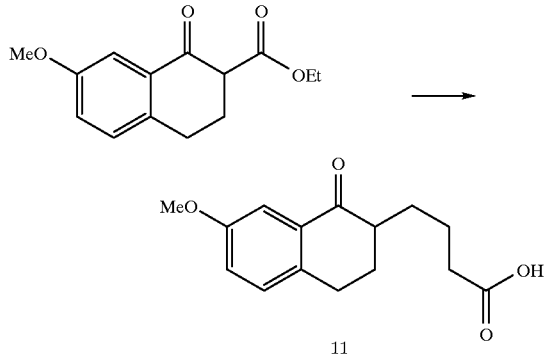

11

2-(Ethoxycarbonyl)-7-methoxy-1-oxo-1,2,3,4-tetrahydronaphthalene (5.0 g, 20.30 mmol) and ethylbromobutyrate (4.47 g, 21.77mmol) were dissolved in anhydrous ethanol (6.0 mL) and heated to reflux. A solution of sodium ethoxide (1.44 g, 20,31 mmol) in anhydrous ethanol (15.0 mL) was then added. The reaction mixture was refluxed for 8 h then enough water was added to dissolve the precipitated NaBr. The remaining ethanol was then removed under vacuo. The residual oil was dissolved in a mixture of methanol (12.0 mL) and water (6.0 mL), then 10 M KOH (6.0 mL) was added. The reaction mixture was refluxed for 24 h. The reaction mixture was then poured into a mixture of 4 M HCl/ice and extracted into CH$_2$Cl$_2$. The organic phase was then washed with water and brine and finally dried over magnesium sulfate. The crude product was recrystallized from cold CCl$_4$ and 3.5 g (66%) of the pure product was isolated as a white solid.

IR (KBr, cm$^{-1}$): 3600–2100 (br, S, CO$_2$H, aromatic, aliphatic ), 1710 (s, ketone or carboxyclic acid) 1680 (s, ketone or carboxyclic acid), 1610, 1500, 1425, 1320, 1270, 1245, 1030; $^1$H NMR (CDCl$_3$): δ 7.50 (d, J=2.4 Hz, 1H), 7.14 (d, J=8.4 Hz, 1H), 7.05 (dd, J=8.4, 2.8 Hz, 1H), 3.83 (s, 3H), 2.94 (t, J=5.2 Hz, 2H), 2.51–2.39 (m, 3H), 2.27–2.20 (m, 1H), 2.03–1.69 (m, 4H), 1.61–1.52 (m, 1H). Anal. calcd for C$_{15}$H$_{18}$O$_4$·0.4 H$_2$O: C, 66.85; H, 7.03. Found: C, 66.74; H, 6.78.

Ethyl 4-(7-methoxy-1-phenylthio-naphthalen-2-yl)-butyrate (12)

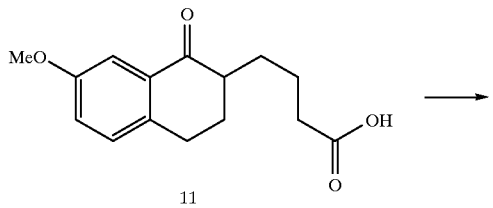

11

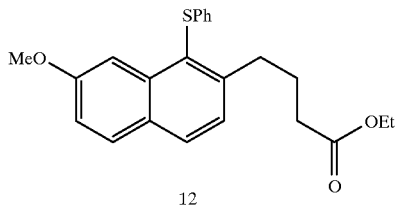

12

4-(7-Methoxy-1-oxo-1,2,3,4-tetrahydronaphthalen-2-yl)-butyric acid 11 (14.3 g, 54.45 mmol) was dissolved in anhydrous ethanol (150 mL) and thiophenol (7.61 mL, 73.87 mmol) was added. The reaction mixture was cooled down to 0° C. and HCl gas was bubbled through the solution until saturation. The reaction mixture was stirred for 24 h at room temperature and then quenched by addition of ice/$H_2O$. The aqueous phase was extracted with ethyl ether (3 times) and dried over magnesium sulfate. Evaporation of the solvent gave a yellow oil that was dissolved in anhydrous dioxane (500 mL) followed by addition of DDQ (12.57 g, 54.26 mmol). The reaction mixture was then refluxed for 2 h. The reaction was cooled down and the hydroquinone was filtered off. The filtrate was then concentrated and redissolved in ethyl ether. The ethereal phase was then washed with 4% NaOH, until neutral and finally dried over magnesium sulfate. The crude product was filtered through a short pad of silica gel to give 17.1 g (83%) of the pure product as white crystals.

IR (KBr, $cm^{-1}$): 3058–2867 (s, aromatic, aliphatic), 1732 (s, carbonyl), 1622, 1582, 1510, 1478, 1456, 1379, 1216, 1033; $^1$H NMR ($CDCl_3$): 7.81 (d, J=8.4 Hz, 1H), 7.79 (d, J=2.4 Hz, 1H), 7.73 (d, J=8.8 Hz, 1H), 7.34 (d, J=8.4 Hz, 1H) 7.14–7.09 (m, 3H), 7.05–7.03 (m, 1H), 6.97–6.93 (m, 2H), 4.10 (q, J=6.8 Hz, 2H), 3.75 (s, 3H), 3.10 (t, J=7.6 Hz, 2H), 2.34 (t, J=7.2 Hz, 2H), 2.01–1.96 (m, 2H), 1.23 (t, J=7.2 Hz, 3H). Anal. calcd for $C_{23}H_{24}O_3S$: C, 72.60; H, 6.36. Found: C, 72.43; H, 6.23.

4-(7-Methoxy-1-phenylthio-naphthalen-2-yl)-2-methyl-pentan-2-ol

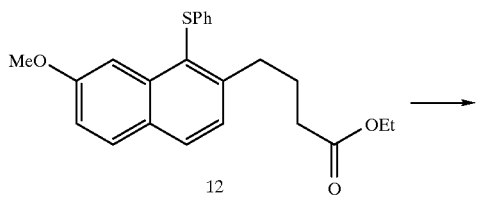

Ethyl 4-(7-methoxy-1-phenylthio-naphthalen-2-yl)-butyrate 12 (17.0 g, 44.68 mmol) was dissolved in a mixture of anhydrous ethyl ether (175 mL) and benzene (175 mL) then MeMgBr (3 M in ethyl ether, 34 mL, 102 mmol) was added dropwise. The reaction mixture was stirred at room temperature for 2 h then quenched by addition of sat. $NH_4Cl$ (aq). Conc. HCl was added until pH=5 then the aqueous phase was extracted with ethyl ether (2 times). The ethereal phase was washed with water (2 times) and brine and dried over magnesium sulfate. Evaporation of the solvent gave 16.3 g (100%) of the pure product that was used for the next step without further purification.

IR (KBr, $cm^{-1}$): 3397 (br, s, OH), 3100–2850 (s, aromatic, aliphatic) 1621, 1509, 1478, 1457, 1439, 1379, 1262, 1231, 1216; $^1$H NMR ($CDCl_3$): 7.81 (d, J=5.2 Hz, 1H), 7.80 (d, J=5.6 Hz, 1H), 7.73 (d, J=8.8 Hz, 1H), 7.34 (d, J=8.4 Hz, 1H), 7.14–7.09 (m, 3H), 7.05–7.01 (m, 1H), 6.97–6.94 (m, 2H), 3.76 (s, 3H), 3.08 (t, J=7.6 Hz, 2H), 1.71–1.63 (m, 2H), 1.53–1.49 (m, 2H), 1.12 (s, 6H). Anal. calcd for $C_{123}H_{26}O_2S.0.5\ H_2O$: C, 73.56; H, 7.25. Found: C, 73.12; H, 7.00.

1,2,3,4-Tetrahydro-1,1-dimethyl-6-methoxy-10-phenylthio-anthracene (13)

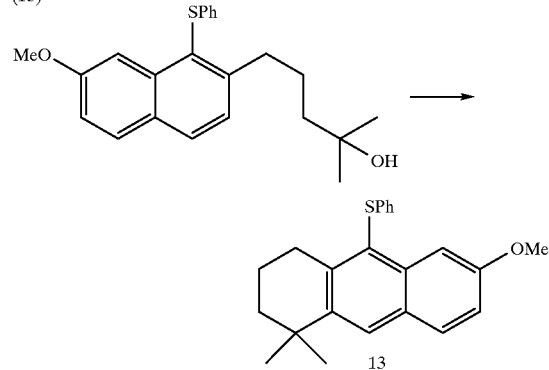

13

4-(7-Methoxy-1-phenylthio-naphthalen-2-yl)-2-methyl-pentan-2-ol (16.3 g, 44.47 mmol) was dissolved in anhydrous ethyl ether (150 mL) and cooled down to 0° C. Conc. $H_2SO_4$ was added and the reaction mixture was stirred at 0° C. for 1 h. This mixture was then poured into a vigorously stirred mixture of water/ice. The product was extracted into EtOAc, then washed with water (2 times), 5% $NaHCO_3$ and brine and finally dried over magnesium sulfate. Evaporation of the solvent gave 15 g (97%) of the title product that was used in the next step without further purification.

IR (neat, $cm^{-1}$): 3050–2866 (aromatic, aliphatic), 1624, 1582, 1493, 1477, 1462, 1439, 1462, 1254, 1241. $^1$H NMR ($CDCl_3$): 7.88 (s, 1H),7.80 (d, J=2.4 Hz, 1H), 7.69 (d, J=8.8 Hz, 1H), 7.16–7.02 (m, 4H) 6.95–6.93 (m, 2H), 3.79 (s, 3H), 3.15 (t, J=6.4 Hz, 2H), 1.85–1.80 (m, 2H), 1.71–1.68 (m, 2H), 1.41 (s, 6H). Anal. calcd for $C_{29}H_{28}O_2.0.6\ H_2O$: C, 83.06; H, 7.02. Found: C, 83.10; H, 7.10.

1, 2, 3, 4-Tetrahydro-1, 1-dimethyl-6-methoxy-anthracene

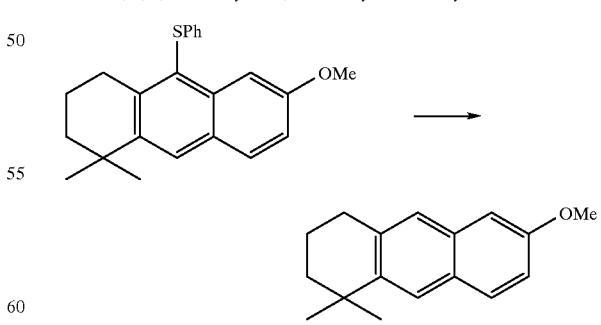

To a soluion of 1,2,3,4-tetrahydro-1,1-dimethyl-6-methoxy-10-phenylthio-anthracene 13 (1.92 g, 5.509 mmol) in anhydrous ethanol (130 mL) was added Raney-Ni (7 mL, 10.5 g, pre-washed 3 times with anhydrous ethanol). The reaction mixture was stirred mechanically at 85° C. (reflux)

for 2 h and then filtered through a pad of Celite at room temperature. Evaporation of ethanol gave a white solid that was dissolved in hot ethyl ether and filtered through a filter paper. The filtrate was concentrated and gave 1.24 (94%) of the title product as a white solid.

IR (KBr, cm$^{-1}$): 3050–2750 (aliphatic, aromatic), 1633, 1603, 1498, 1458, 1397, 1255, 1214, 1159, 1026; $^1$H NMR (CDCl$_3$): 7.71 (s, 1H), 7.64 (d, J=8.8 Hz, 1H), 7.42 (s, 1H), 7.03 (dd, J=9.2, 2.4 Hz, 1H) 7.00 (d, J=2.4 Hz, 1H), 3.89 (s, 3H), 2.96 (t, J=6.4 Hz, 2H), 1.90–1.84 (m, 2H), 1.75–1.72 (m, 2H), 1.38 (s, 6H). Anal. calcd for C$_{17}$H$_2$O.0.2 H$_2$O : C, 83.70; H, 8.43. Found: C, 83.91; H, 8.42.

1, 2, 3, 4-Tetrahydro-1, 1-dimethyl-6-hydroxy-anthracene

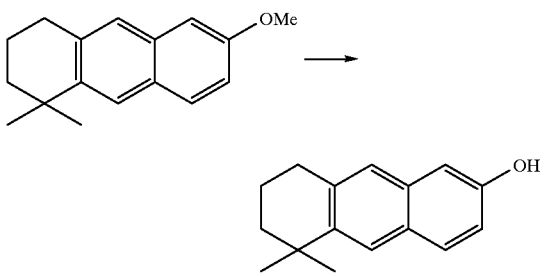

1,2,3,4-Tetrahydro-1,1-dimethyl-6-methoxy-anthracene (670 mg, 2.788 mmol) was dissolved in anhydrous CH$_2$Cl$_2$ (18 mL) and BBr$_3$ (1 M in CH$_2$Cl$_2$, 9.90 mL, 9.90 mmol) was added dropwise. The reaction mixture was stirred at room temperature for 1.5 h and was then quenched by addition of 1 M HCl. The phases were separated and the aqueous phase extracted with EtOAc (3 times). The combined organic phases were then dried over magnesium sulfate. The crude product was purified by flash chromatography on silica gel (EtOAc/hexane 10/90) to give 610 mg (97%) of the title product as a brownish solid.

IR (KBr, cm$^{-1}$): 3250 (s, OH), 3000–2863 (aromatic, aliphatic), 1637, 1606, 1501, 1457, 1317, 1189, 1151; $^1$H NMR (CDCl$_3$): 7.71 (s, 1H), 7.65 (d, J=8.8 Hz, 1H), 7.36 (s, 1H), 7.00 (d, J=1.6 Hz, 1H) 6.98 (dd, J=8.8, 2.8 Hz, 1H), 2.95 (t, J=6.4 Hz, 2H), 1.90–1.84 (m, 2H), 1.75–1.72 (m, 2H), 1.38 (s, 6H). Anal. calcd for C$_{16}$H$_{18}$O.0.1 H$_2$O: C, 84.24; H, 8.04. Found: C, 84.06; H, 8.19.

1, 2, 3, 4-Tetrahydro-1, 1-dimethyl-6-trifluoromethanesulfonyloxy-anthracene (14)

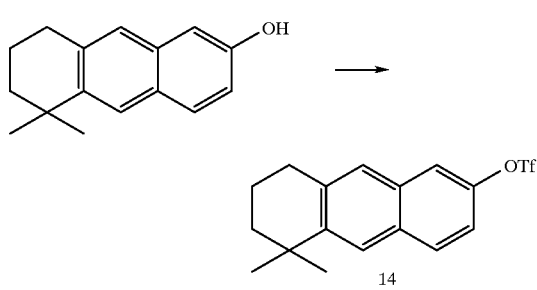

1,2,3,4-Tetrahydro-1,1-dimethyl-6-hydroxy-anthracene (6.98 g, 30.84 mmol) was dissolved in pyridine (300 mL) and cooled down to 0° C. Triflic anhydride (11.2 mL, 65.85 mmol) was added dropwise and the reaction mixture stirred at room temperature for 2 h. This was then poured into a mixture of 1 M HCl and ice and the product was extracted into EtOAc (2 times). The organic extracts were then combined, washed with water and 1 M HCl and dried over magnesium sulfate. The crude product was filtered through a pad of silica gel to give 11.0 g (100%) of the title product as a yellow solid.

IR (KBr, cm$^{-1}$): 3050–2875 (aromatic, aliphatic), 1605, 1499, 1418, 1395, 1247, 1212, 1141; $^1$H NMR (CDCl$_3$): 7.83 (s, 1H), 7.82 (d, J=9.6 Hz, 1H), 7.59 (d, J=2.4 Hz, 1H), 7.56 (s, 1H), 7.24 (dd, J=9.2, 2.4 Hz, 1H), 3.00 (t, J=6.4 Hz, 2H), 1.92–1.86 (m, 2H), 1.77–1.74 (m, 2H), 1.40 (s, 6H).

Methyl 4-(5, 6, 7,8-tetrahydro-5, 5-dimethyl-anthracen-2-yl)-benzoate

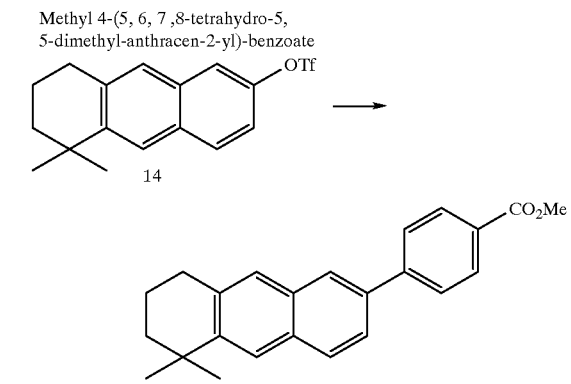

1,2,3,4-Tetrahydro-1,1-dimethyl-6-trifluoromethanesulfonyloxy-anthracene 14 (5.0 g, 13.95 mmol) was dissolved in degassed NMP (100 mL), then Pd$_2$(dba)$_3$ (522 mg, 0.284 mmol), CuI (264 mg, 1.39 mmol), LiCl (1.74 g, 10.03 mmol), Ph$_3$As (679 mg, 1.132 mmol) and methyl 4-tributylstannylbenzoate (6.41 g, 16.80 mmol) were added. The reaction mixture was stirred at 65° C. for 3 h. Water and EtOAc were then added and the phases were separated. The aqueous phase was extracted with EtOAc (3 times) and the combined organic phases were dried over magnesium sulfate. The crude product was purified by flash chromatography on silica gel (EtOAc/hexane 5/95). The solid product obtained after flash chromatography was further washed with hexane to remove the traces of tin by-products. The title material was isolated (4 g, 83%) as an off white solid.

IR (KBr, cm$^{-1}$): 3025–2851 (aromatic, aliphatic), 1714 (carbonyl), 1607, 1437, 1288, 1277, 1191, 1112. $^1$H NMR (CDCl$_3$): 8.13 (d, J=8.4 Hz, 2H), 7.94 (d, J=1.4 Hz, 1H), 7.83 (d, J=8.6 Hz, 1H), 7.82 (s, 1H), 7.77 (d, J=8.4 Hz, 2H), 7.64 (dd, J=8.5, 1.7 Hz, 1H), 7.59 (s, 1H), 3.95 (s, 3H), 3.00 (t, J=6.3 Hz, 2H), 1.91–1.87 (m, 2H), 1.78–1.75 (m, 2H), 1.41 (s, 6H).

Methyl 4-(5, 6, 7, 8-tetrahydro-8-oxo-5, 5-dimethyl-anthracen-2-yl)-benzoate (15)

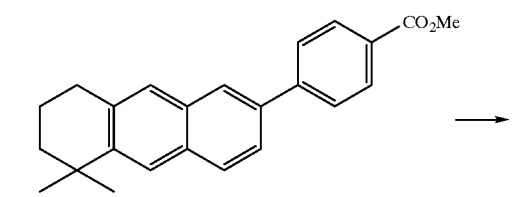

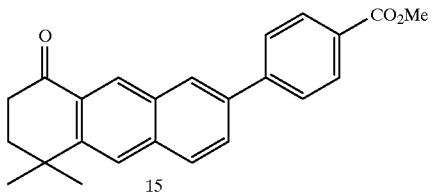

Methyl 4-(5,6,7,8-tetrahydro-5,5-dimethyl-anthracen-2-yl)-benzoate (400 mg, 1.16 mmol) was dissolved in benzene (20.0 mL) and cooled down to 10° C. Celite (1.75 g), PDC (2.18 g, 5.75 mmol) and t-BuO$_2$H (70% in water, 520 mg, 5.74 mmol) were then added. The reaction mixture was stirred at room temperature for 7 h and an additional portion of benzene (20.0 mL), celite (1.75 g), PDC (2.18 g, 5.75 mmol) and t-BuO$_2$H (70% in H$_2$O, 520 mg, 5.74 mmol) were added and the reaction was stirred for another 7 h. The reaction mixture was filtered through a pad of celite and concentrated to give 322 mg (77%) of the pure ketone as white crystals.

IR (KBr, cm$^{-1}$): 3025–2863 (aromatic, aliphatic), 1713 (carbonyl), 1687 (carbonyl), 1606, 1403, 1289, 1275, 1191, 1109; $^1$H NMR (CDCl$_3$): 8.67 (s, 1H), 8.18 (s, 1H), 8.16 (d, J=8.4 Hz, 2H), 7.93 (d, J=8.8 Hz, 1H), 7.86 (s, 1H), 7.84 (dd, J=8.8, 2.0 Hz, 1H), 7.78 (d, J=8.4 Hz, 2H),3.96 (s, 3H), 2.85 (t, J=6.8 Hz, 2H), 2.11 (t, J=6.8 Hz, 2H), 1.51 (s, 6H).

Methyl 4-(5, 6-dihydro-8-trifluoromethanesulfonyloxy-5, 5-dimethyl-anthracen-2-yl)-benzoate (16)

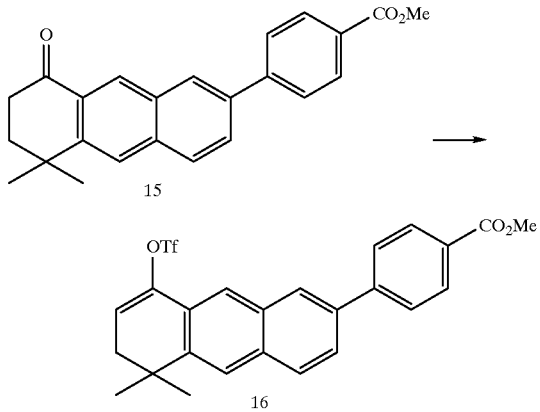

Methyl 4-(5,6,7,8-tetrahydro-8-oxo-5,5-dimethyl-anthracen-2-yl)-benzoate 15 (322 mg, 0.90 mmol) was dissolved in CH$_2$Cl$_2$ (7.0 mL) and cooled down to 0° C. 2,6-Di-tert-butyl-4-methylpyridine (277 mg, 1.35 mmol) and Tf$_2$O (180 µL, 1.063 mmol) were then added. The reaction mixture was stirred at room temperature for 18 h. The reaction was then concentrated and redissolved in EtOAc. The organic phase was washed with water and dried over magnesium sulfate. Evaporation of the solvent gave the crude title product as a brownish solid that was washed with hexane to give 420 mg (95%) of an off white solid.

IR (KBr, cm$^{-1}$): 3100–2875 (aromatic, aliphatic), 1723 (carbonyl), 1607, 1416, 1287, 1274, 1245, 1217, 1139, 1101, 1070; $^1$H NMR (CDCl$_3$): 8.16 (d, J=8.4 Hz, 2H), 8.10 (s, 1H), 7.89 (d, J=10.8 Hz, 2H), 7.80–7.75 (m, 4H), 6.10 (t, J=4.8 Hz, 1H), 3.96 (s, 3H), 2.50 (d, J=5.2 Hz, 2H), 1.43 (s, 6H).

Methyl 4-(5, 6-dihydro-5, 5-dimethyl-8-(p-methoxy-phenyl)-anthracen-2 yl)-benzoate (9B)

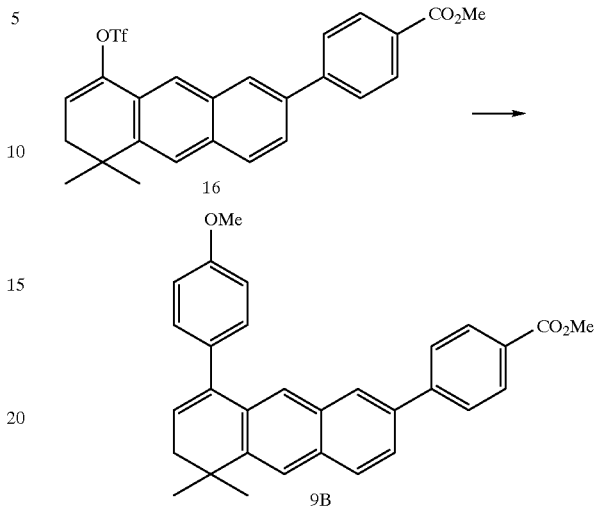

Methyl 4-(5,6-dihydro-8-trifluoromethanesulfonyloxy-5, 5-dimethyl-anthracen-2-yl)-benzoate 16 (420 mg, 0.86 mmol) was dissolved in degassed NMP (7 mL) then Pd$_2$(dba)$_3$ (34 mg, 0.017 mmol), CuI (17 mg, 0.089 mmol), LiCl (108 mg, 2.55 mmol), Ph$_3$As (41 mg, 0.069 mmol) and 4-methoxy-tributylstannylbenzene (410 mg, 1.03 mmol) were added. The reaction mixture was stirred at 65° C. for 3 h. Water and EtOAc were then added and the phases were separated. The aqueous phase was extracted with EtOAc (3 times) and the combined organic phases were dried over magnesium sulfate. The crude product was purified by flash chromatography on silica gel (EtOAc/hexane 5/95). The solid product obtained after flash chromatography was further washed with hexane to remove traces of tin by-products. The title material was obtained (200 mg, 52%) as an off white solid.

IR (KBr, cm$^{-1}$): 3050–2833 (aromatic, aliphatic), 1707 (carbonyl), 1608, 1512, 1463, 1437, 1286, 1244. $^1$H NMR (CDCl$_3$): 8.10 (d, J=8.0 Hz, 2H), 7.90 (s, 1H), 7.87 (d, J=8.4 Hz, 1H), 7.78 (s, 1H), 7.73 (d, J=8.4 Hz, 2H), 7.69 10 (d, J=8.8 Hz, 1H), 7.53 (s, 1H), 7.36 (d, J=8.8 Hz, 2H), 6.98 (d, J=8.4 Hz, 2H), 6.05 (t, J=4.8 Hz, 1H), 3.94 (s, 3H), 3.88 (s, 3H), 2.42 (d, J=4.8 Hz, 2H), 1.46 (s, 6H).

4-(5, 6-Dihydro-5, 5-dimethyl-8-(4-methoxy-phenyl)-anthracen-2-yl)-benzoic acid (IB)

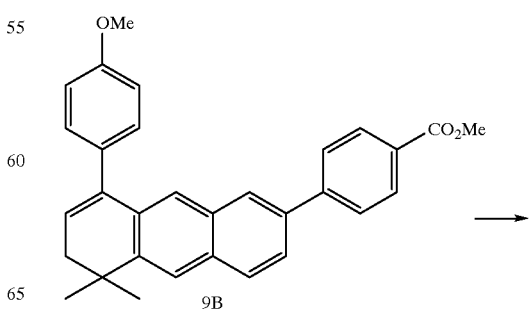

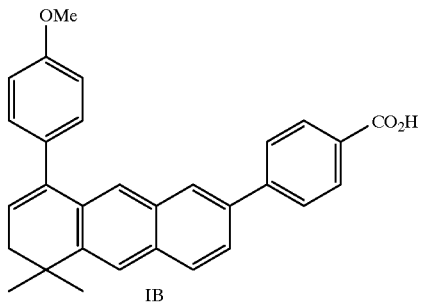

IB

Methyl 4-(5,6-dihydro-5,5-dimethyl-8-(p-methoxyphenyl)-anthracen-2-yl)-benzoate 9B (70 mg, 0.156 mmol) was dissolved in a mixture of THF (2.0 mL) and ethanol (2.0 mL) and then 5 M KOH (195 μL) was added. The reaction mixture was stirred at room temperature for 16 h. The reaction was then diluted with water and the product was precipitated by addition of 2 M HCl. The precipitate was filtered off and the solid washed with water. The crude product could then, if necessary, be purified by recrystallization from either EtOAc/hexane or $CH_2Cl_2$/ethanol to give the pure title material (29 mg, 43%).

IR (KBr, $cm^{-1}$): 3500–2400 (br s, carboxyclic acid, aromatic, aliphatic), 1685 (carbonyl), 1607, 1510, 1287, 1244, 1176. $^1$H NMR (DMSO-$d_6$): δ 8.14 (s, 1H), 7.99 (d, J=8.4 Hz, 2H), 7.98 (d, J=8.0 Hz, 1H), 7.92 (d, J=8.4 Hz, 2H), 7.89 (s, 1H), 7.83 (dd, J=8.8, 1.6 Hz, 1H), 7.51 (s, 1H), 7.32 (d, J=8.8 Hz, 2H), 7.02 (d, J=8.8 Hz, 2H), 6.04 (t, J=4.4 Hz, 1H), 3.81 (s, 3H), 2.38 (d, J=4.4 Hz, 2H),1.40 (s, 6H). MS: 433.2 (M–H)$^-$.

EXAMPLE 3

4-(5, 6-Dihydro-5, 5-dimethyl-8-(4-hydroxy-phenyl)-anthracen-2-yl)-benzoic acid (IC)

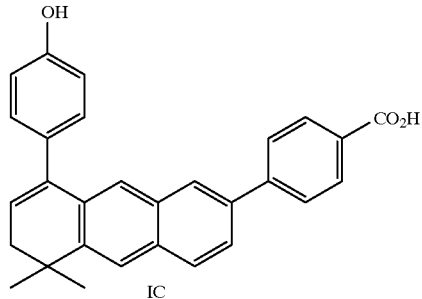

IC

Methyl 4-(5, 6-dihydro-5, 5-dimethyl-8-(p-acetoxy-phenyl)-anthracen-2-yl)-benzoate (9C)

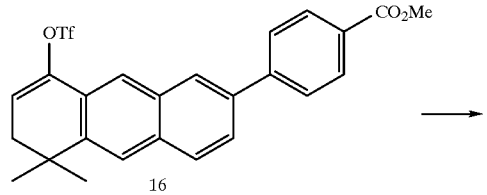

16

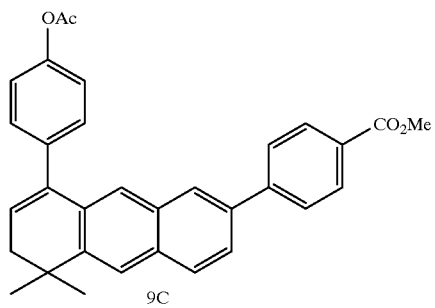

9C

The title material was prepared as described in Example 2 by reaction of methyl 4-(5,6-dihydro-8-trifluoromethanesulfonyloxy-5,5-dimethyl-anthracen-2-yl)-benzoate 16 with 4-acetoxy-tributylstannylbenzene instead of 4-methoxy-tributylstannylbenzene.

$^1$H NMR ($C_6D_6$): 8.23 (2H, d, J=8.2 Hz), 7.76 (1H, s), 7.71 (1H, s), 7.70 (2H, br d), 7.54 (1H, s), 7.49 (1H, dd, J=8.5 and 1.8 Hz), 7.40 (2H, d, J=8.3 Hz), 7.38–7.36 and 7.18–7.15 (2 x 2H, 2 m), 5.88 (1H, t, J=4.7 Hz), 3.56 (3H, s), 2.18 (2H, d, J=4.7 Hz), 1.79 (3H, s), 1.39 (6H, s).

4-(5, 6-Dihydro-5, 5-dimethyl-8-(4-hydroxy-phenyl)-anthracen-2-yl)-benzoic acid (IC)

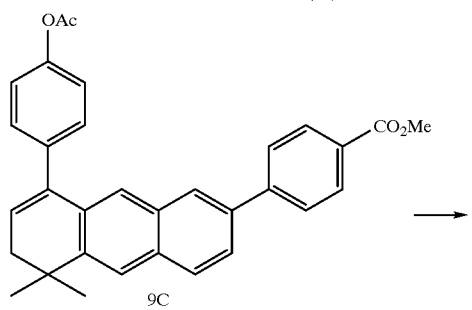

9C

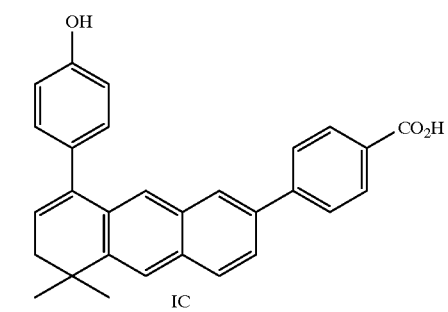

IC

The title material was obtained by saponification of methyl 4-(5,6-dihydro-5,5-dimethyl-8-(p-acetoxy-phenyl)-anthracen-2-yl)-benzoate 9C as described in Example 2.

IR (KBr, $cm^{-1}$): 3421 (OH), 3600–2500 (br s, carboxyclic acid, aromatic, aliphatic), 1684, 1653, 1607, 1507, 1261. $^1$H NMR (DMSO-$d_6$): 8.14 (s, 1H), 7.99 (d, J=8.4 Hz, 2H), 7.97 (d, J=7.6 Hz, 1H), 7.93 (d, J=8.4 Hz, 2H), 7.88 (s, 1H), 7.83 (d, J=8.4 Hz, 1H), 7.53 (s, 1H), 7.20 (d, J=8.4 Hz, 2H), 6.84 (d, J=8.0 Hz, 2H), 6.00 (t, J=4.8 Hz 1H), 2.36 (d, J=4.4 Hz, 2H),1.40 (s, 6H). MS: 419.3 (M–H)$^-$.

EXAMPLE 4

4-(5, 6-Dihydro-5, 5-dimethyl-8-(4-methyl-phenyl)-anthracen-2-yl)-benzoic acid (ID)

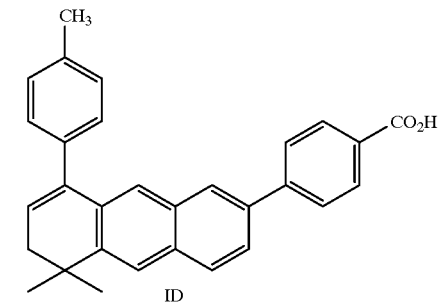

Methyl 4-(5, 6-dihydro-5, 5-dimethyl-8-(4-methyl-phenyl)-anthracen-2-yl)-benzoate 9D

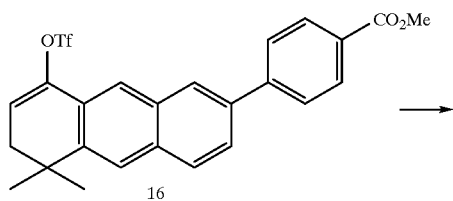

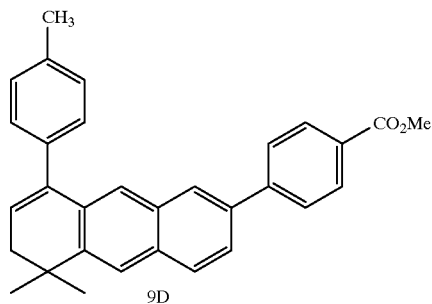

The title material was prepared as described in Example 2 by reaction of methyl 4-(5,6-dihydro-8-trifluoromethanesulfonyloxy-5,5-dimethyl-anthracen-2-yl)-benzoate 16 with 4-methyl-tributylstannylbenzene instead of 4-methoxy-tributylstannylbenzene.

IR (KBr, cm$^{-1}$): 3100–2900 (aromatic, aliphatic), 1717 (carbonyl), 1608, 1431, 1283, 1179, 1104. $^1$H NMR (CDCl$_3$): 8.10 (d, J=8.4 Hz, 2H), 7.90 (s, 1H), 7.87 (d, J=8.4 Hz, 1H), 7.78 (s, 1H), 7.73 (d, J=8.4 Hz, 2H), 7.69 (dd, J=8.4, 2.0 Hz, 1H), 7.53 (s, 1H), 7.33 (d, J=8.0 Hz 2H), 7.25 (d, J=8.0 Hz, 2H), 6.07 (t, J=4.8 Hz, 1H), 3.94 (s, 3H), 2.44 (s, 3H), 2.42 (d, J=4.8 Hz, 2H), 1.46 (s, 6H).

4-(5, 6-Dihydro-5, 5-dimethyl-8-(4-methyl-phenyl)-anthracen-2-yl)-benzoic acid (ID)

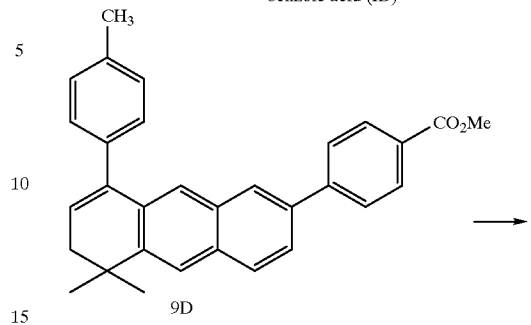

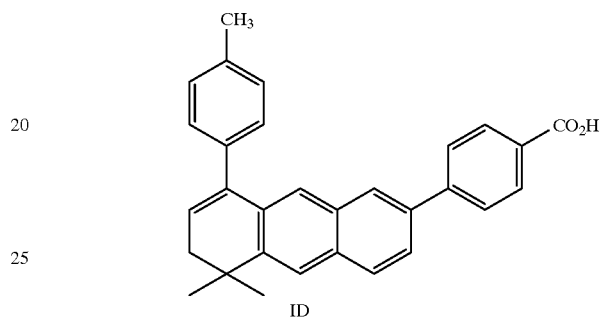

The title material was obtained by saponification of methyl 4-(5,6-dihydro-5,5-dimethyl-8-(4-methyl-phenyl)-anthracen-2-yl)-benzoate 9D as described in Example 2.

IR (KBr, cm$^{-1}$): 3500–2500 (br s, carboxyclic acid, aromatic, aliphatic), 1683, 1605, 1424, 1292. $^1$H NMR (DMSO-d$_6$): 8.14 (s, 1H), 7.99 (d, J=8.4 Hz, 2H), 7.98 (d, J=8.8 Hz, 1H), 7.93 (d, J=8.4 Hz, 2H), 7.89 (s, 1H), 7.84 (dd, J=8.8, 1.6 Hz, 1H), 7.50 (s, 1H), 7.30–7.22 (m, 4H), 6.06 (t, J=4.8 Hz 1H), 2.38 (d, J=6.8 Hz, 2H), 2.37 (s, 3H), 1.41 (s, 6H). MS: 417.3 (M–H)$^-$.

EXAMPLE 5

4-(5, 6-Dihydro-5, 5-dimethyl-8-(3, 3-dimethyl-1-butyn-1-yl)-anthracen-2-yl)-benzoic acid (IE)

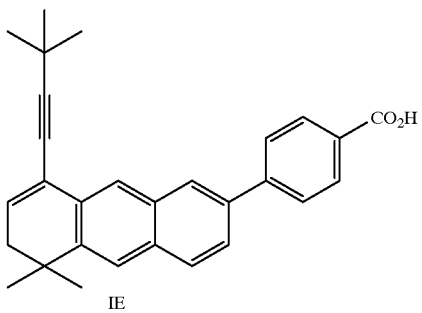

Methyl 4-(5, 6-dihydro-5, 5-dimethyl-8-(3, 3-dimethyl-1-butyn-1-yl)-anthracen-2-yl)-benzoate (PE)

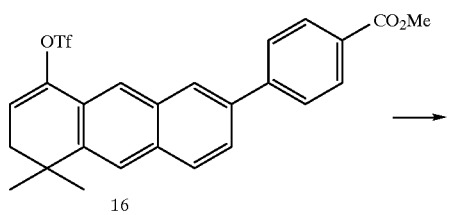

16

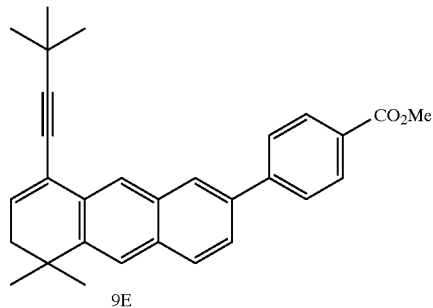

9E

Methyl 4-(5,6-dihydro-8-trifluoromethanesulfonyloxy-5,5-dimethyl-anthracen-2-yl)-benzoate 16 (125 mg, 0.255 mmol) was dissolved in THF (7.0 mL) and cooled down to 0° C. The solution was degassed with Ar then 3,3-dimethyl-1-butyne (95 μL, 0.766 mmol), Pd(PPh$_3$)$_2$Cl$_2$ (12 mg, 0.017 mmol), CuI (14 mg, 0.0735 mmol) and diisopropylamine (0.86 mL, 6.13 mmol) were added. The reaction mixture was stirred at 0° C. for 30 min. The reaction mixture was then extracted with EtOAc (3 times) and the combined organic extracts were washed with water, 1 M HCl and brine and finally dried over magnesium sulfate. Evaporation of the solvent gave the crude product that was washed with hexane. The pure product (108 mg, 100%) was isolated as an off-white solid.

IR (KBr, cm$^{-1}$): 3010–2800 (aromatic, aliphatic), 1720 (carbonyl), 1606, 1436, 1287, 1271, 1110.

4-(5,6-Dihydro-5,5-dimethyl-8-(3,3-dimethyl-1-butyn-1-yl)-anthracen-2-yl)-benzoic acid (IE)

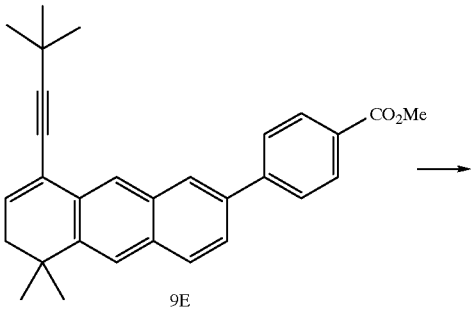

9E

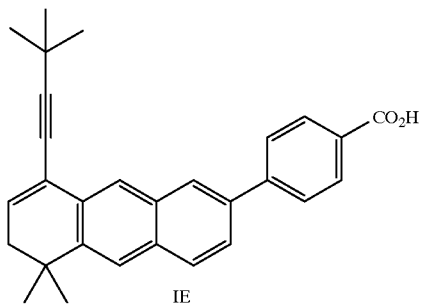

IE

The title material was obtained by saponification of methyl 4-(5,6-dihydro-5,5-dimethyl-8-(3,3-dimethyl-1-butyn-1-yl)-anthracen-2-yl)-benzoate 9E as described in Example 2.

IR (KBr, cm$^{-1}$): 3500–2375 (carboxyclic acid, aromatic, aliphatic), 1681 (carbonyl), 1605, 1419, 1315, 1296, 1282. $^1$H NMR (DMSO-d$_6$): 8.29 (s, 1H), 8.07–8.05 (m, 3H), 8.01–7.98 (m, 3H), 7.88–7.86 (m, 2H) 6.41 (dd, J=4.8, 4.4 Hz, 1H), 2.36 (d, J=4.8 Hz, 2H), 1.39 (s, 9H), 1.34 (s, 6H). MS: 407 (M–H)$^-$. Anal. calcd for C$_{29}$H$_{28}$O$_2$.0.6 H$_2$O: C, 83.06; H, 7.02. Found: C, 83.10; H, 7.10.

EXAMPLE 6

4-(5,6-Dihydro-5,5-dimethyl-8-(2-tert-butyl-thio)-anthracen-2-yl)-benzoic acid (IF)

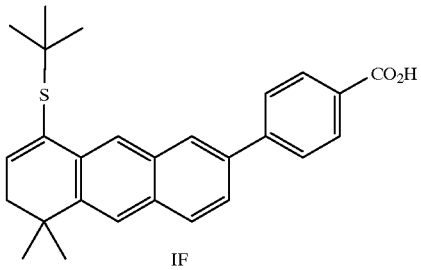

IF

Methyl 4-(5,6-dihydro-5,5-dimethyl-8-(2-tert-butyl-thio)-anthracen-2-yl)-benzoate (9F)

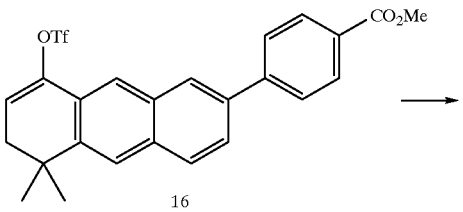

16

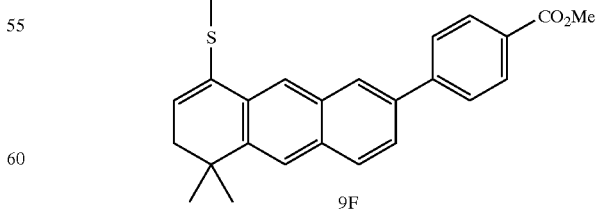

9F

A suspension of the potassium salt of t-butylsulfide (71 mg, 0.553 mmol) in THF (3.5 mL) and benzene (3.5 mL) was degassed with Ar, then the triflate (150 mg, 0.306 mmol)

and Pd(PPh$_3$)$_4$ were added. The reaction mixture was stirred at room temperature for 10 min and then at 65° C. for 30 min. The reaction was diluted with EtOAc and then washed with water, NaHCO$_3$, water and brine and finally dried over magnesium sulfate. The crude product was purified by silica gel (EtOAc/hexane 10/90). The pure fractions were collected and gave 55 mg (42%) of the pure product as an off white solid.

IR (KBr, cm$^{-1}$): 3050–2850 (aromatic, aliphatic), 1718 (carbonyl), 1606, 1433, 1362, 1288, 1274, 1113. $^1$H NMR (CDCl$_3$): 8.54 (s, 1H), 8.14 (d, J=8.4 Hz, 2H), 8.11 (s, 1H), 7.86 (d, J=8.4 Hz, 1H), 7.80 (d, J=8.4 Hz, 2H), 7.72 (s, 1H), 7.70 (dd, J=8.4, 1.6 Hz, 1H), 6.63 (t, J=4.4 Hz, 1H), 3.96 (s, 3H), 2.44 (d, J=4.4 Hz, 2H), 1.43 (s, 6H), 1.35 (s, 9H).

4-(5,6-Dihydro-5,5-dimethyl-8-(2-tert-butyl-thio)-anthracen-2-yl)-benzoic acid (IF)

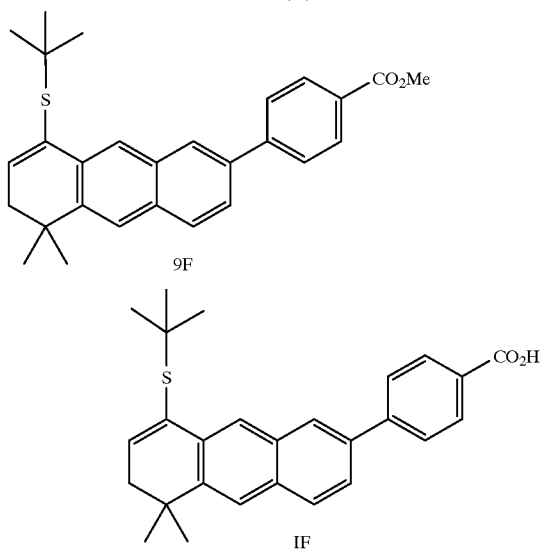

The title material was obtained by saponification of methyl 4-(5,6-dihydro-5,5-dimethyl-8-(tert-butylthio)-anthracen-2-yl)-benzoate 9F as described in Example 2.

IR (KBr, cm$^{-1}$): 3650–2400 (carboxyclic acid, aromatic, aliphatic), 1684, 1608, 1426, 1362, 1315, 1293, 1184; $^1$H NMR (DMSO-d$_6$): 8.49 (s, 1H), 8.34 (s, 1H), 8.04 (d, J=8.0 Hz, 2H), 7.98 (d, J=7.6 Hz, 2H) 7.98 (d, J=7.6 Hz, 2H), 7.98 (d, J=7.6 Hz, 1H), 7.85 (d, J=8.0 Hz, 1H), 7.84 (s, 1H), 6.63 (dd, J=4.4, 4.4 Hz, 1H), 2.43 (d, J=4.8 Hz, 2H), 1.38 (s, 6H), 1.30 (s, 9H). MS: 415 (M–H)$^-$. HRMS: Calc for C$_{27}$H$_{27}$O$_2$S: 415.17319. Found: 415.17190.

EXAMPLE 7

4-(5,6-Dihydro-5,5-dimethyl-8-(furan-2-yl)-anthracen-2-yl)-benzoic acid (IG)

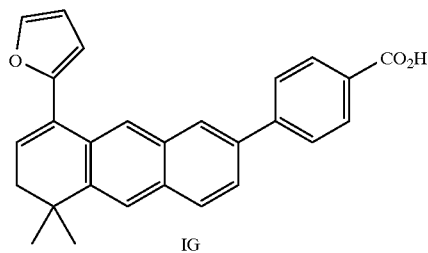

Methyl 4-(5,6-dihydro-5,5-dimethyl-8-(furan-2-yl)-anthracen-2-yl)-benzoate (9G)

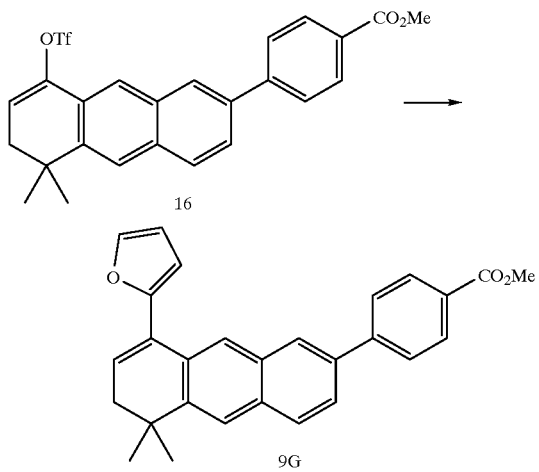

The title material was prepared as described in Example 2 by reaction of methyl 4-(5,6-dihydro-8-trifluoromethanesulfonyloxy-5,5-dimethyl-anthracen-2-yl)-benzoate 16 with 2-tributylstannylfuran instead of 4-methoxy-tributylstannylbenzene.

$^1$H NMR (C$_6$D$_6$): 8.26 (2H, d, J=8.3 Hz), 8.16 (1H, s), 7.76 (1H, br s), 7.73 (1H, s), 7.69 (1H, d, J=8.5 Hz), 7.51 (1H, dd, J=8.5 and 1.9 Hz), 7.46 (2H, d, J=8.4 Hz), 7.27 (1H, d, J=1.9 Hz), 6.50 (1H, d, J=3.2 Hz), 6.44 (1H, t, J=5.0 Hz), 6.30 (1H, dd, J=3.3 and 1.8 Hz), 3.58 (3H, s), 2.13 (2H, d, J=5.0 Hz), 1.30 (6H, s).

4-(5,6-dihydro-5,5-dimethyl-8-(furan-2-yl)-anthracen-2-yl)-benzoic acid (IG)

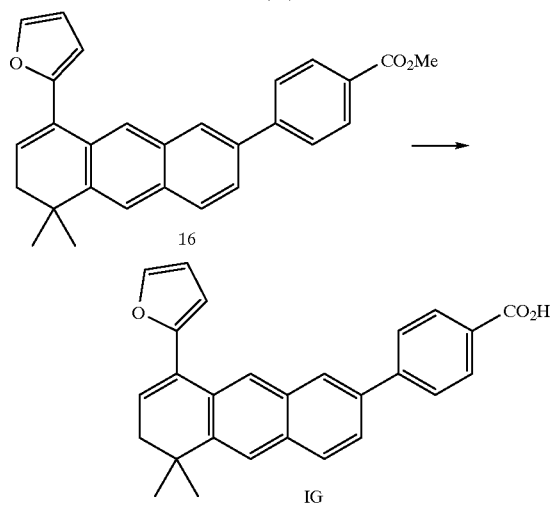

The title material was obtained by saponification of methyl 4-(5,6-dihydro-5,5-dimethyl-8-(furan-2-yl)-anthracen-2-yl)-benzoate 9G as described in Example 2.

IR (KBr, cm$^{-1}$): 1685, 1607; $^1$H NMR (DMSO-d$_6$): 8.31 (1H, s), 8.06–8.00 (4H, m), 7.97 (2H, d, J=8.4 Hz), 7.92 (1H, s), 7.88 (1H, dd, J=8.6 and 1.7 Hz), 7.78 (1H, s), 6.73 (1H, d, J=3.2 Hz), 6.64 (1H, dd, J=3.2 and 1.9 Hz), 6.51 (1H, t), 2.40 (2H, d, J=5.0 Hz), 1.38 (6H, s). MS: 393.05 (M–H)$^-$.

EXAMPLE 8

4-(5,6-Dihydro-5,5-dimethyl-8-(pyridin-3-yl)-anthracen-2-yl)-benzoic acid (IH)

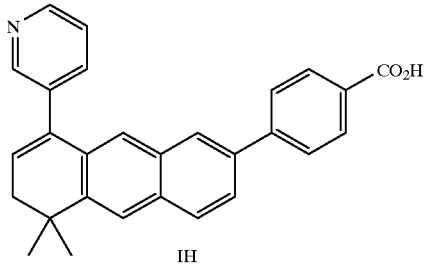

IH

Methyl 4-(5,6-dihydro-5,5-dimethyl-8-(pyridin-3-yl)-anthracen-2-yl)-benzoate (9H)

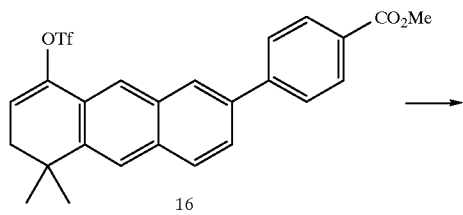 

16

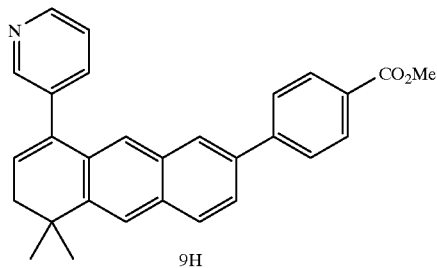

9H

The title material was prepared as described in Example 2 by reaction of methyl 4-(5,6-dihydro-8-trifluoromethanesulfonyloxy-5,5-dimethyl-anthracen-2-yl)-benzoate 16 with 3-tributylstannylpyridine instead of 4-methoxy-tributylstannylbenzene.

$^1$H NMR (C$_6$D$_6$): 8.63 (1H, s), 8.21 (1H, s), 8.03 (2H, d, J=8.5 Hz), 8.01 (1H, d, J=8.4 Hz), 7.97 (2H, d, J=8.4 Hz), 7.94 (1H, s), 7.87 (1H, dd, J=8.5 and 1.3 Hz), 7.83 (1H, br dt, J=7.8 Hz), 7.51 (1H, dd, J=7.6 and 4.7 Hz), 7.47 (1H, s), 6.21 (1H, t, J=4.7 Hz), 3.88 (3H, s), 2.45 (2H, d, J=4.7 Hz), 1.43 (6H, s).

4-(5,6-Dihydro-5,5-dimethyl-8-(pyridin-3-yl)-anthracen-2-yl)-benzoic acid (IH)

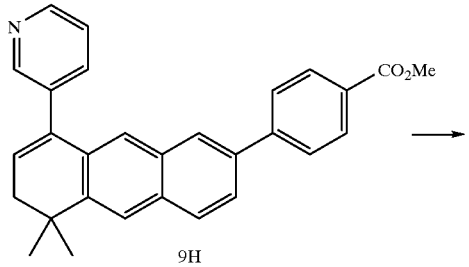 

9H

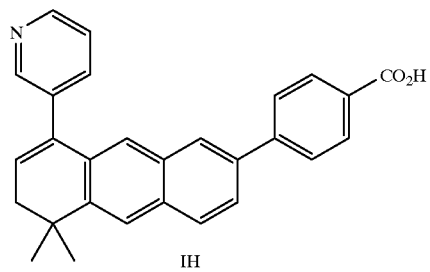

IH

The title material was obtained by saponification of methyl 4-(5,6-dihydro-5,5-dimethyl-8-(pyridin-3-yl)-anthracen-2-yl)-benzoate 9H as described in Example 2.

IR (KBr, cm$^{-1}$): 1683, 1607; $^1$H NMR (DMSO-d$_6$): 8.64–8.63 (2H, m), 8.20 (1H, s), 8.02–7.92 (6H, m), 7.86 (1H, dd, J=8.5 and 1.7 Hz), 7.83 (1H, dt, J=7.8 and 1.9 Hz), 7.51 (1H, dd, J=7.6 and 4.8 Hz), 7.47 (1H, s), 6.21 (1H, t, J=4.7 Hz), 2.45 (2H, d, J=4.7 Hz), 1.40 (6H, s). MS: 404.14 (M–H)$^-$. Anal. calcd for C$_{28}$H$_{23}$NO$_2$.0.4 HCl: C, 80.06; H, 5.61; N, 3.33. Found: C, 80.05; H, 5.62; N, 3.33.

We claim:

1. A compound having the formula

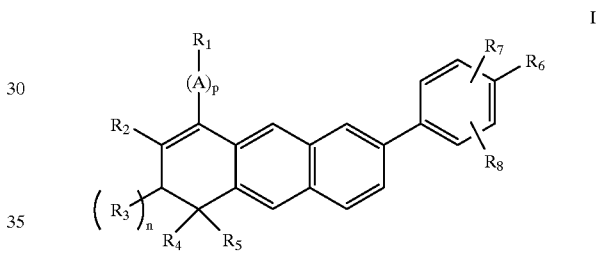

I or nontoxic pharmaceutically acceptable salts, physiologically hydrolyzable esters or solvates thereof, in which A is —O(CH$_2$)$_m$—, —S(O)$_q$(CH$_2$)$_m$—, —NR$_9$(CH$_2$)$_m$—, —C≡C—, —CR$_9$R$_{10}$, —CR=CR$_{10}$—, phenyl, naphthyl or heteroaryl, said phenyl, naphthyl or heteroaryl group being optionally substituted by 1 to 3 identical or different C$_{1-6}$alkyl, C$_{1-6}$alkoxy, halogen, —(CH$_2$)$_m$CO$_2$R$_9$, —(CH$_2$)$_m$CF$_3$, —(CH$_2$)$_m$CN, —(CH$_2$)$_m$N$_3$,—(CH$_2$)$_m$OR$_9$, —(CH$_2$)$_m$NR$_9$R$_{10}$, or —COR$_9$ groups;

R$_1$ is C$_{1-6}$alkyl, C$_{3-6}$cycloalkyl, —OSO$_2$CF$_3$, —OCOR$_{11}$, —OPO(OR$_{11}$)$_2$, halogen, aryl or heteroaryl, said aryl or heteroaryl group being optionally substituted by 1–3 identical or different C$_{1-6}$alkyl, C$_{1-6}$alkoxy, halogen, —(CH$_2$)$_a$CO$_2$R$_{11}$, —(CH$_2$)$_a$CF$_3$, —(CH$_2$)$_a$CN, —(CH$_2$)$_a$N$_3$, —(CH$_2$)$_a$OR$_{11}$, —(CH$_2$)$_a$NR$_{11}$R$_{12}$ or —COR$_{11}$, groups;

R$_2$ and R$_3$ are each independently hydrogen, C$_{1-6}$alkyl, C$_{2-6}$alkenyl or C$_{2-6}$alkynyl, but when n is 1, R$_2$ and R$_3$ together can form a radical of the formula

;

R$_4$ and R$_5$ are each independently hydrogen or C$_{1-6}$alkyl;
R$_6$ is —CO$_2$R$_{13}$, —C$_{1-6}$alkyl, —CH$_2$OH, —CONHR$_{13}$, —SO$_3$H, —PO$_3$H or —CHO;

$R_7$ and $R_8$ are each independently hydrogen, halogen, $C_{1-6}$alkyl, hydroxy, $C_{1-6}$alkyloxy, —CN, —$N_3$ or nitro;

$R_9$, $R_{10}$, $R_{11}$ and $R_{12}$ are each independently hydrogen, $C_{1-6}$alkyl or trifluoromethyl;

$R_{13}$ is hydrogen, $C_{1-6}$alkyl, allyl, benzyl, p-methoxybenzyl, trichloroethyl or trimethylsilylethyl;

n and p are 0 or 1; m, q and a are 0 to 2.

2. A compound of the formula

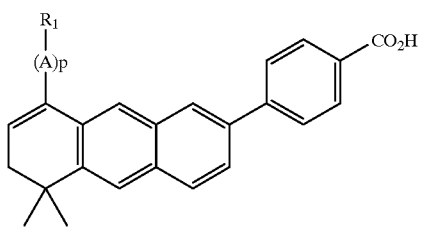

wherein A is —S(O)$_q$(CH$_2$)$_m$—, —C≡C—, —CR$_9$R$_{10}$, —CR$_9$=CR$_{10}$—, phenyl, naphthyl or heteroaryl, said phenyl, naphthyl or heteroaryl group being optionally substituted by 1 to 3 identical or different $C_{1-6}$alkyl, $C_{1-6}$alkoxy, halogen, —(CH$_2$)$_m$CO$_2$R$_{11}$, —(CH$_2$)$_m$CF$_3$, —(CH$_2$)$_m$CN, —(CH$_2$)$_m$N$_3$, —(CH$_2$)$_m$OR$_9$, —(CH$_2$)$_m$NR$_9$R$_{10}$, or —COR$_9$ groups;

$R_1$ is $C_{1-6}$alkyl, $C_{3-6}$cycloalkyl, —OSO$_2$CF$_3$, —OCOR$_{11}$, —OPO(OR$_{11}$)$_2$, halogen, aryl or heteroaryl, said aryl or heteroaryl group being optionally substituted by 1–3 identical or different $C_{1-6}$alkyl, $C_{1-6}$alkoxy, halogen, —(CH$_2$)$_a$CO$_2$R$_{11}$, —(CH$_2$)$_a$CF$_3$, —(CH$_2$)$_a$CN, —(CH$_2$)$_a$N$_3$, —(CH$_2$)$_a$OR$_{11}$, —(CH$_2$)$_a$NR$_{11}$R$_{12}$ or —COR$_{11}$ groups;

$R_9$, $R_{10}$, $R_{11}$ and $R_{12}$ are each independently hydrogen, $C_{1-6}$alkyl or trifluoromethyl;

$R_{13}$ is hydrogen, $C_{1-6}$alkyl, allyl, benzyl, p-methoxybenzyl, trichloroethyl or trimethylsilylethyl;

p is 0 or 1; m, q and a are 0 to 2; or a nontoxic pharmaceutically acceptable salt, physiologically hydrolyzable ester or solvate thereof.

3. The compound of the formula

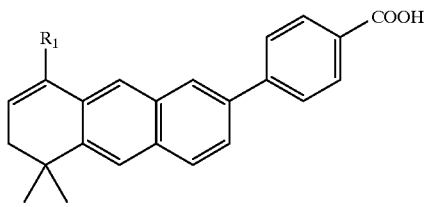

wherein $R_1$ is phenyl, p-methoxyphenyl, p-hydroxyphenyl, p-methylphenyl, 3,3-dimethyl-1-butyn-1-yl, tert-butylthio, m-hydroxyphenyl, 2-furanyl, 3-pyridinyl, or a nontoxic pharmaceutically acceptable salt, physiologically hydrolyzed ester or solvate thereof.

4. A compound of the formula

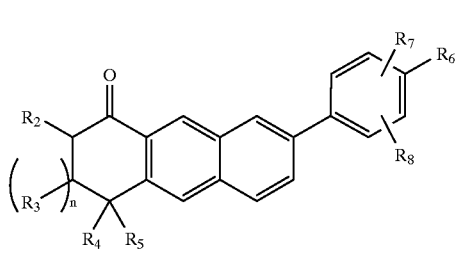

wherein $R_2$ and $R_3$ are each independently hydrogen, $C_{1-6}$alkyl, $C_{2-6}$alkenyl or $C_{2-6}$alkynyl, but when n is 1, $R_2$ and $R_3$ together can form a radical of the formula

$R_4$ and $R_5$ are each independently hydrogen or $C_{1-6}$alkyl;

$R_6$ is —CO$_2$R$_{13}$, —$C_{1-6}$alkyl, —CH$_2$OH, —CONHR$_{13}$, —SO$_3$H, —PO$_3$H or —CHO;

$R_7$ and $R_8$ are each independently hydrogen, halogen, $C_{1-6}$alkyl, hydroxy, $C_{1-6}$alkyloxy, —CN, —$N_3$ or nitro;

$R_{13}$ is hydrogen, $C_{1-6}$alkyl, allyl, benzyl, p-methoxybenzyl, trichloroethyl or trimethylsilylethyl; and n is 0 or 1.

5. A method for treating in a host mammal, one or more of the diseases and conditions selected from the group consisting of chronic skin inflammatory diseases, rheumatic diseases, non-malignant proliferative skin conditions and malignant tumors, which comprises administering to said host an effective therapeutic amount of a compound of claim 1 or a pharmaceutical composition thereof.

6. A method for the minimization or prevention of a post-surgical adhesion formation between organ surfaces comprising administering to an animal host an effective amount of a compound of claim 1 for a period of time sufficient to permit tissue repair.

7. The method of claim 5 wherein the compound administered is the compound of claim 3.

8. A pharmaceutical composition comprising a therapeutically effective amount of a compound of claim 1 and a pharmaceutically acceptable carrier.

* * * * *